(12) United States Patent
Potyrailo et al.

(10) Patent No.: US 11,867,676 B2
(45) Date of Patent: Jan. 9, 2024

(54) MULTI-GAS SENSING SYSTEM AND METHOD

(71) Applicant: General Electric Company, Schenectady, NY (US)

(72) Inventors: Radislav Alexandrovich Potyrailo, Niskayuna, NY (US); Richard St. Pierre, Clifton Park, NY (US); Bruce Courtney Amm, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 868 days.

(21) Appl. No.: 16/812,613

(22) Filed: Mar. 9, 2020

(65) Prior Publication Data

US 2021/0278384 A1    Sep. 9, 2021

(51) Int. Cl.
*G01N 33/00* (2006.01)

(52) U.S. Cl.
CPC ..... *G01N 33/0031* (2013.01); *G01N 33/0006* (2013.01)

(58) Field of Classification Search
CPC .............. G01N 33/0031; G01N 33/0006
See application file for complete search history.

(56) References Cited

U.S. PATENT DOCUMENTS

| 4,911,892 | A | 3/1990 | Grace |
| 5,933,245 | A | 8/1999 | Wood |
| 7,053,425 | B2 | 5/2006 | Sandvik |
| 7,171,312 | B2 | 1/2007 | Steinthal |
| 7,763,208 | B2 | 7/2010 | Steichen |
| 9,304,101 | B1 | 4/2016 | Farber |
| 9,638,653 | B2 | 5/2017 | Potyrailo |
| 9,678,030 | B2 | 6/2017 | Potyrailo |
| 10,060,872 | B1 | 8/2018 | Potyrailo |
| 2015/0323510 | A1* | 11/2015 | Huynh ............... G01N 33/0031 73/23.34 |
| 2016/0187277 | A1 | 6/2016 | Potyrailo |

(Continued)

OTHER PUBLICATIONS

Potyrailo, "Multivariable Sensors for Ubiquitous Monitoring of Gases in the Era of Internet of Things and Industrial Internet", Chem. Rev., Sep. 7, 2016, vol. 116, Issue 19, pp. 11877-11923.

(Continued)

*Primary Examiner* — Herbert K Roberts
*Assistant Examiner* — Anthony W Megna Fuentes
(74) *Attorney, Agent, or Firm* — Fletcher Yoder, P.C.

(57) ABSTRACT

A multi-gas sensing system includes a sensing circuit comprising one or more sensing elements. Each sensing element includes a sensing material configured to detect at least one gas analyte. A management circuit is configured to excite the sensing elements with an alternating current at at least one predetermined frequency. The management circuit measures one or more electrical responses of the sensing elements responsive to exciting the sensing elements with the alternating current. The management circuit determines one or more characteristics of the sensing circuit. One or more processors receive the electrical responses of the sensing elements and the characteristics of the sensing circuit. The one or more processors determine a concentration of the at least one gas analyte based on the electrical responses of the sensing elements and the characteristics of the sensing circuit.

24 Claims, 11 Drawing Sheets

(56) References Cited

U.S. PATENT DOCUMENTS

| | | |
|---|---|---|
| 2019/0204291 A1 | 7/2019 | Potyrailo |
| 2019/0234896 A1* | 8/2019 | Andersson ......... G01N 33/0014 |
| 2019/0257803 A1* | 8/2019 | Brown ................ G01N 27/123 |

OTHER PUBLICATIONS

J. Smulko, "The Measurement Setup for Gas Detection by Resistance Fluctuations of Gas Sensors", IEEE, Mar. 12, 2007, pp. 2028-2031.

Fadel, T. R.; Farrell, D. F.; Friedersdorf, L. E.; Griep, M. H.; Hoover, M. D.; Meador, M. A.; Meyyappan, M. Toward the Responsible Development and Commercialization of Sensor Nanotechnologies, ACS Sens. 2016, 1, 207-216.

Janasek, D.; Franzke, J.; Manz, A. Scaling and the design of miniaturized chemical-analysis systems, Nature 2006, 442, 374-380.

Lewis, A.; Edwards, P. Validate personal air-pollution sensors, Nature 2016, 535, 29-31.

Fahad, H. M.; Shiraki, H.; Amani, M.; Zhang, C.; Hebbar, V. S.; Gao, W.; Ota, H.; Hettick, M.; Kiriya, D.; Chen, Y.-Z. Room temperature multiplexed gas sensing using chemical-sensitive 3.5-nm-thin silicon transistors, Sci. Adv. 2017, 3, e1602557.

Kalantar-Zadeh, K.; Berean, K. J.; Ha, N.; Chrimes, A. F.; Xu, K.; Grando, D.; Ou, J. Z.; Pillai, N.; Campbell, J. L.; Brkljača, R. A human pilot trial of ingestible electronic capsules capable of sensing different gases in the gut, Nat. Electron. 2018, 1, 79.

Schipani, F.; Miller, D.; Ponce, M.; Aldao, C.; Akbar, S.; Morris, P. Electrical Characterization of Semiconductor Oxide-Based Gas Sensors Using Impedance Spectroscopy: A Review, Rev. Adv. Sci. Eng. 2016, 5, 86-105.

Cooks, R. G.; Ouyang, Z.; Takats, Z.; Wiseman, J. M. Ambient mass spectrometry, Science 2006, 311, 1566-1570.

Wolfbeis, O. S. Probes, Sensors, and Labels: Why is Real Progress Slow?, Angew. Chem. Int. Ed. 2013, 52, 9864-9865.

Allen, D. T.; Torres, V. M.; Thomas, J.; Sullivan, D. W.; Harrison, M.; Hendler, A.; Herndon, S. C.; Kolb, C. E.; Fraser, M. P.; Hill, A. D.; Lamb, B. K.; Miskimins, J.; Sawyer, R. F.; Seinfeldi, J. H. Measurements of methane emissions at natural gas production sites in the United States, Proc. Natl. Acad. Sci. U.S.A. 2013, 110, 17768-17773.

McManus, J. B.; Zahniser, M. S.; Nelson, D. D.; Shorter, J. H.; Herndon, S. C.; Jervis, D.; Agnese, M.; McGovern, R.; Yacovitch, T. I.; Roscioli, J. R. Recent progress in laser-based trace gas instruments: performance and noise analysis, Appl. Phys. B 2015, 119, (1), 203-218.

Zhang, L.; Tian, G.; Li, J.; Yu, B. Applications of absorption spectroscopy using quantum cascade lasers, Appl. Spectrosc. 2014, 68, (10), 1095-1107.

Fitch, J. P.; Raber, E.; Imbro, D. R. Technology Challenges in Responding to Biological or Chemical Attacks in the Civilian Sector, Science 2003, 302, 1350-1354.

Potyrailo, R. A.; Surman, C.; Nagraj, N. N.; Burns, A. Materials and Transducers Toward Selective Wireless Gas Sensing, Chem. Rev. 2011, 111, 7315-7354.

* cited by examiner

MULTI-GAS SENSING SYSTEM AND METHOD

GOVERNMENT LICENSE RIGHTS

This invention was made with government support under contract 75D30118C02617 awarded by the National Institute For Occupational Safety And Health. The government has certain rights in the invention.

FIELD

One or more embodiments are disclosed that relate to systems and methods for sensing multiple gases with a sensing system.

BACKGROUND

Complex environments, such as industrial, urban, or battlefield, contain many different gases. While typical gas sensors provide continuous monitoring capabilities, they typically have poor detection selectivity of a particular gas over others. Additionally, existing sensors are designed to provide a single output per sensor. Therefore, in order to sense multiple different gases, multiple different sensors are needed, making the gas sensor system difficult to calibrate and preserve the calibration over time upon exposure to the complex environments.

Additionally, instruments based on traditional analytical technologies, such as gas chromatography, mass spectrometry, ion mobility spectrometry, and tunable diode laser absorption spectroscopy are preferred when detection selectivity and accuracy are essential, despite their limitations of relatively high power consumption, narrow dynamic range of sensing, cost, and size. These instruments are often inconvenient and costly, even with a reduced carrier gas, vacuum, or power demands, but are an unavoidable alternatively to existing sensor systems.

Known wearable personal multi-gas monitors or systems include different types of sensors for specific gases. Such designs require multiple sensor elements and lead to an increase in power consumption and need dedicated electronics for each of the sensors. Additionally, each sensor requires its own calibration function stored onboard the personal multi-gas monitor.

BRIEF DESCRIPTION

In one or more embodiments, a multi-gas sensing system includes a sensing circuit comprising one or more sensing elements. Each of the one or more sensing elements includes a sensing material configured to detect at least one gas analyte. A management circuit is configured to excite the one or more sensing elements with an alternating current at at least one predetermined frequency. The management circuit measures one or more electrical responses of the one or more sensing elements responsive to exciting the one or more sensing elements with the alternating current at the at least one predetermined frequency. The management circuit determines one or more characteristics of the sensing circuit. One or more processors receive the one or more electrical responses of the one or more sensing elements and the one or more characteristics of the sensing circuit. The one or more processors determine a concentration of the at least one gas analyte based on the one or more electrical responses of the one or more sensing elements and the one or more characteristics of the sensing circuit.

In one or more embodiments, a multi-gas sensing system includes a sensing circuit comprising plural sensing elements. Each of the sensing elements includes a sensing material configured to detect at least one gas analyte. A first element includes sensing electrodes coating with the sensing material and positioned on a substrate, and a second sensing element is a mechanical resonator coated with the sensing material. A management circuit is configured to excite the sensing elements with an alternating current at at least one predetermined frequency. The management circuit includes an impedance analyzer configured to measure electrical responses of the sensing elements based on different detection principles. The impedance analyzer measures a response of the first sensing element at one or more frequencies at a dielectric relaxation peak of the sensing material, and the impedance analyzer measures a resonant peak frequency position of the second sensing element.

In one or more embodiments, a multi-gas sensing system includes a sensing circuit comprising one or more sensing elements. Each of the one or more sensing elements includes a sensing material configured to detect at least one gas analyte. A management circuit is configured to excite the one or more sensing elements with an alternating current at at least one predetermined frequency. The management circuit measures one or more electrical responses of the one or more sensing elements responsive to exciting the one or more sensing elements with the alternating current at the at least one predetermined frequency. The management circuit determines one or more characteristics of the sensing circuit. One or more processors receive the one or more electrical responses of the one or more sensing elements and the one or more characteristics of the sensing circuit. The one or more processors determine a concentration of the at least one gas analyte based on the one or more electrical responses of the one or more sensing elements and the one or more characteristics of the sensing circuit. The one or more processors configured to determine whether the concentration of the at least one gas analyte exceeds a predetermined threshold, and determine a responsive action of one or more of an asset or a subject responsive to determining that the concentration of the at least one gas analyte exceeds the predetermined threshold.

DETAILED DESCRIPTION

Figure 1:
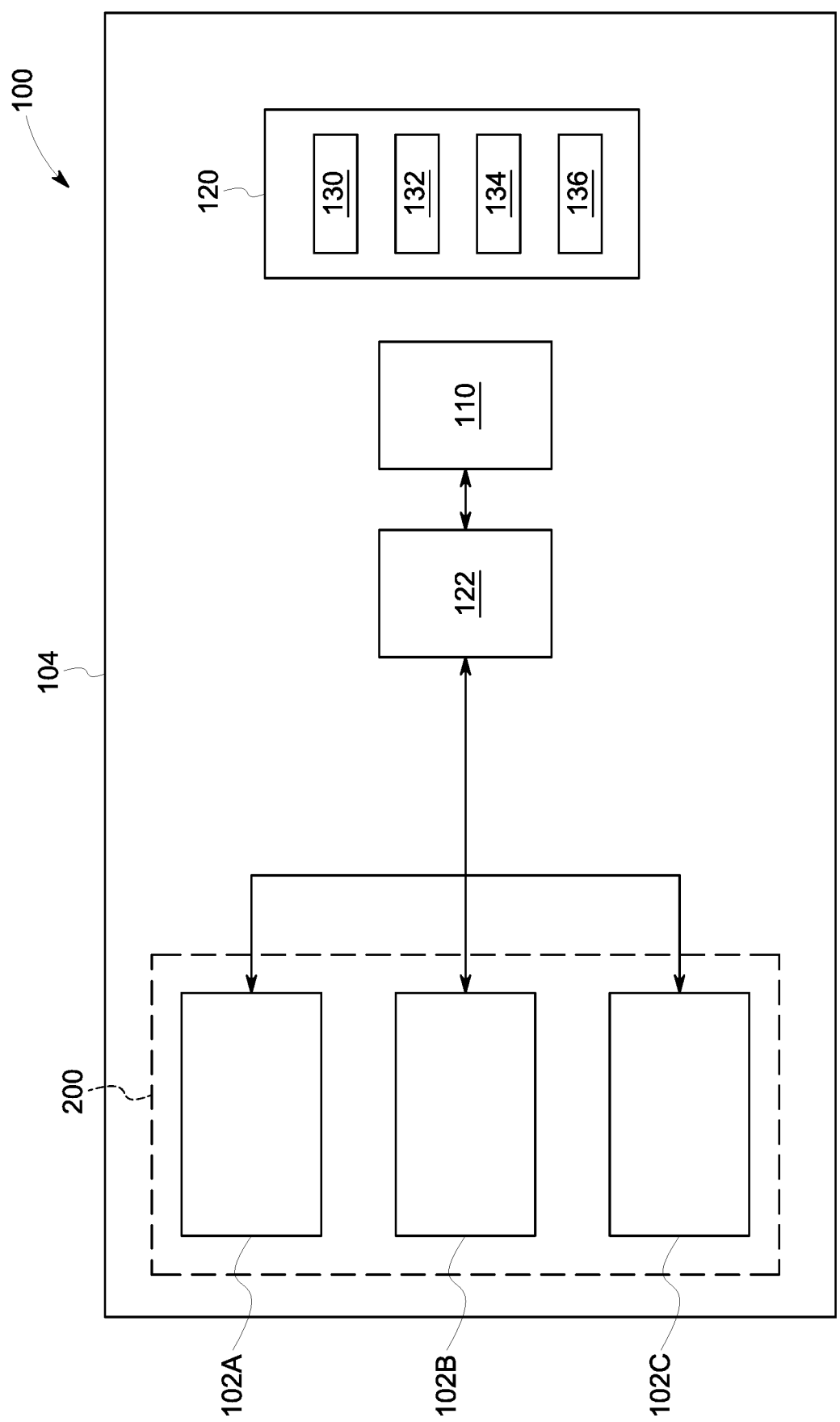
FIG. 1 illustrates one embodiment of a multi-gas sensing system in accordance with one embodiment.

One or more embodiments of the inventive subject matter described herein provide multi-gas sensing systems and methods that include a sensing circuit having one or more sensing elements where each sensing element may detect one or more gas analytes and discriminate two or more gases such as analyte gases and interferent gases. The multi-gas sensing system includes at least one sensing element that may detect, discriminate, or otherwise sense different gases relative to each other sensing element. For example, the single sensing circuit may detect, discriminate, or otherwise sense several gases. For multi-gas detection, the sensing elements may be resistor-capacitor RC electrical circuits with R and C components that may be changed either by the presence of the gases or by electronic control of the circuit, such as by the management circuit or the system controller.

A management circuit may excite the sensing elements with an alternating current at a predetermined discrete or separate frequency or predetermined frequency range. The system measures electrical responses of the sensing elements responsive to alternating electrical current applied to the sensing elements at one or more different discrete frequencies, one or more different frequency ranges, and/or one or more different resistor-capacitor configurations, of the sensing elements. One or more processors may determine one or more characteristics of the sensing circuit. For example, the characteristics may include temperatures of the sensing elements, ambient conditions of an area proximate the multi-gas sensing system, resistor-capacitor RC configurations of the sensing elements, or the like.

The one or more processors may determine a concentration of the gas analyte based on the electrical responses of the sensing elements and the characteristics of the sensing circuit. For example, the one or more processors may analyze the data using one or more statistical methods, such as, but not limited to Support Vector Machine, Principal Component Analysis, or any alternative multivariable transfer functions, the determine the concentration of one or more gases. In one or more embodiments, the system may include one or more multivariable transducers with independent outputs that may be used to recognize different gas responses from a single sensing material.

The multi-gas sensing system may be a wearable device that may be worn or move from one place to another by an operator. The multi-gas sensing system may be positioned in or be an integrated part of a helmet, hat, glove, or other clothing attributes. For example, the system may be held within a wearable or non-wearable transferable object, such as a frame of military or industrial eyeglasses, a wearable pulse oximeter, a safety vest or harness, an article of clothing, a mobile device (e.g., a cellular phone, a tablet, or the like), or the like. The wearable device may be integrated into a fabric of the clothing, can be positioned on clothing such as on a pocket, can be in a form of an arm band, worn on a wrist or other extremity, or the like. The wearable device can be fabricated using manufacturing technologies based on flexible electronics and other known approaches to provide conformal and flexible designs, implementations, and use. Optionally, the system may be a stationary device, may be independently mobile (e.g., detachable from an operator and capable of moving independent of the operator), may be airborne, or the like.

The multi-gas sensing system may include a sensing element that may detect or otherwise sense different gases. For example, the single sensing circuit may detect several different gases. For multi-gas detection, the sensing element may be a resistor-capacitor (RC) electrical circuit with R and C components that may be changed either by the presence of the gases or by electronic control of the circuit, such as by the management system or the system controller. The system measures electrical responses of the sensing element responsive to alternating electrical current applied to the sensing element at one or more different frequencies, one or more different frequency ranges, and/or one or more different resistor-capacitor configurations of the sensing element.

The one or more sensing elements may include a sensing material that responds to different gases. One or more multivariable transducers with independent outputs may be used to recognize different gas responses from the same sensing material. For example, a solution for gas sensing may be based on multivariable detection. Design criteria for the individual sensors include a sensing material that responds to different gases and a multivariable transducer having independent outputs to recognize different gas responses from the sensing material.

In one or more embodiment, the system 100 may be a wearable device, may be stationary, may be independently mobile (e.g., detachable from an operator and capable of moving independent of the operator), airborne, or the like.

At least one technical effect of the various embodiments herein includes a multi-gas sensing system that may accurately detect one or several different gases present in an environment with a single type of sensor. The single type of sensor may include a single type of sensing element that operates at different conditions. Nonlimiting examples of these conditions include different constant and/or variable temperature, different RC electrical circuit parameters, or the like. The resistor-capacitor configurations of the different sensing elements may be changed in order for the same type of sensing element to sense or otherwise detect different gases, different concentrations of different gases, or the like. The resistor-capacitor configurations may be changed by the presence of different gases, or by electronic control of the sensing circuit. The multi-gas sensing system may accurately detect a single gas with plural sensor outputs, with a multivariable transducer that may produce independent outputs to recognize different gas responses from the sensing material of each sensing element. Additionally, the multi-gas sensing system may correct for any undesirable environmental effects.

FIG. 1 illustrates one embodiment of a multi-gas sensing system 100. The multi-gas sensing system 100 examines fluid in contact with the system 100. The fluid may be a gas, a liquid, a gas-liquid mixture, a solid, particles or particulate matter, or the like, containing one or more analyte gases therein. In another embodiment, the fluid may be a gas or fuel, such as a hydrocarbon-based fuel. One example of the fluid is natural gas that is supplied to a powered system (e.g., a vehicle, or a stationary generator set) for consumption. Other examples of such a fluid can include gasoline, diesel fuel, jet fuel or kerosene, bio-fuels, petrodiesel-biodiesel fuel blends, natural gas (liquid or compressed), and fuel oils. Another example of the fluid is indoor or outdoor ambient air. Another example of the fluid is air at an industrial, residential, military, construction, urban, and any other known site. Another example of the fluid is ambient air with relatively small concentrations of benzene, naphthalene, carbon monoxide, ozone, formaldehyde, nitrogen dioxide, sulfur dioxide, ammonia, hydrofluoric acid, hydrochloric acid, phosphine, ethylene oxide, carbon dioxide, hydrogen sulfide, chemical warfare agents such as nerve, blister, blood, and choking agents, hydrocarbons and/or other pollutants. Another example of the fluid is ambient air with relatively small concentrations, medium concentrations, and large concentrations of flammable or combustible gases such as methane, ethane, propane, butane, hydrogen, and/or other gases. Another example of the fluid is at least one gas dissolved in an industrial liquid such as transformer oil, bioprocess media, fermentation media, wastewater, and any other. Another example of the fluid is the at least one gas dissolved in a consumer liquid such as milk, non-alcoholic beverages, alcoholic beverages, cosmetics, and any other. Another example of the fluid is at least one gas dissolved in a body liquid such as blood, sweat, tears, saliva, urine, and any other.

The multi-gas sensing system 100 may be in contact with the fluid in the form of a fluid vessel (not shown) that may be a form of a vessel with controlled volume or in the form of an open area such as an indoor facility (e.g., a room, a hall, a house, a school, a hospital, a confined space, or the like), or in the form of an outdoor facility (e.g., a stadium, a gas-production site, fueling stations, gasoline fueling stations, hydrogen fueling stations, compressed natural gas fueling stations, liquefied natural gas fueling stations, gas distribution site, fuel distribution site, a seashore, a forest, or the like). In one embodiment, the sensing system 100 may provide continuous monitoring of the fluid within the reservoir or flow path. In one or more embodiments, the sensing system 100 may be an impedance gas sensor, an electromagnetic sensor, a photonic sensor, an electronic sensor, a hybrid sensor, or another type of sensor. Optionally, the multivariable gas sensor may be a sensor array.

Figure 3:
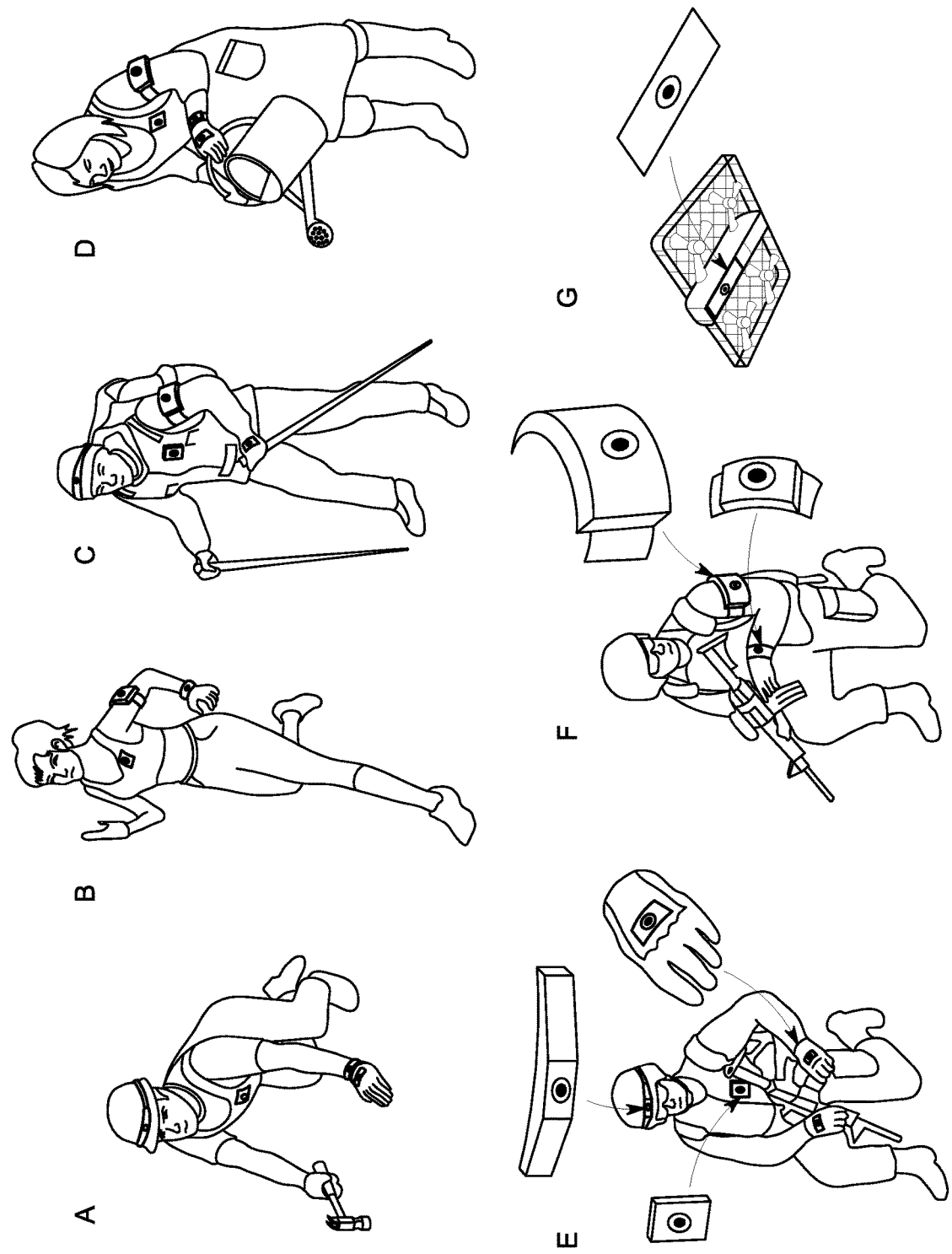
FIG. 3 illustrates exemplary positions of a wearable multi-gas sensing system in accordance with one embodiment.

In one or more embodiments, the sensing system 100 may be a wearable sensor system, may be held within a wearable and/or non-wearable transferrable object (e.g., a frame of military or industrial eyeglasses), or the like. The wearable device may be worn by a subject, such as a human or animal, may be removably coupled or integrated with an article worn by a subject (e.g., a shirt, pants, safety vest, safety personal protection clothing, eyeglasses, hat, helmet, hearing device, or the like), or may be any alternative device that may be transferrable such that sensor can be moved between different positions, may be stationary or substantially stationary, or the like. In one or more embodiments, a substrate or circuit board 104 of the sensing system 100 may have an area that is less than 5000 square millimeters (mm²), less than 2000 mm², less than 1000 mm², less than 500 mm², or the like. FIG. 3 illustrates exemplary positions of different wearable sensing system 100. For example, the wearable sensing system may be worn, or otherwise carried, by different subjects or individuals, such as, but not limited to, soldiers, medical professionals, athletes, system operators, otherwise active or inactive individuals, or the like. Optionally, the wearable sensing system may be coupled with, integrated with, disposed on, or the like, an asset, such as a moving system such as a drone, a stationary system, or the like. The wearable systems may be positioned on items worn by the subject, such as helmets, pockets (e.g., of shirts, pants, bags, or the like), gloves, arm bands, ear pieces, or the like, or may be attached or otherwise coupled directly to the subject or asset, such as on the wrist, around an ankle, or the like.

The multi-gas sensing system 100 may represent one or more different versions of sensing systems described herein. The system 100 includes a sensing circuit 200, a modifier assembly 122, and a management circuit 110 that may control operation of the modifier assembly 122 and the sensing circuit 200. In one or more embodiments, the sensing circuit 200 may be a resistor-capacitor RC electrical circuit that includes one or more resistor R and capacitor C components that may be changed by the presence of one or more analyte gases of interest. For example, the management circuit 110 may change the resistance and/or capacitance of the sensing circuit 200. In one or more embodiments, the circuitry of the sensing system 100 may be able to perform impedance measurements of the sensing system 100 to determine an impedance response to one or more analyte gases of interest. Impedance measurements may be performed at one or more different frequencies or at one or more different RC configurations of the sensing circuit 200. For example, the sensing circuit 200 of the sensing system 100 may measure impedance responses of the sensing system 100 at different frequencies, at different resistances of the RC electrical circuit, at different capacitances of the RC electrical circuit, or any combination of two or more therein.

The term impedance as used herein may be a non-limiting term for any electrical response of the sensing system to an alternating electrical current applied to the sensing system. Such response may be measured as different electrical properties. Nonlimiting examples of these commonly measured different electrical responses of the sensing system to alternating electrical current include impedance, admittance, reactance, susceptance, or the like. In the present specification, examples of the responses are given as impedances, however, other electrical responses of the sensing system to alternating electrical current may be also equally produced.

In one embodiment, the electrical response of the sensing system may be monitored at the gas-modulated front shoulder of the dielectric relaxation peak of the sensing material.

Measurements of the impedance of the sensing system 100 may be performed at a single frequency, at discrete frequencies, or at multiple scanned frequencies by an impedance analyzer or impedance analyzer circuit that may be a part of or coupled with the management circuit 110 and/or a system controller 120, and conductively coupled with the sensing circuit 200. Optionally, the management circuit 110 of the multi-gas sensing system 100 may also or alternatively be called a spectrum analyzer, analyzer, alternating electrical current response analyzer, or the like.

In one or more embodiments, the impedance analyzer may be a part of the management circuit 110 and may measure electrical responses of at least two sensing elements of the multi-gas sensing system, where the two sensing elements are based on different detection principles. A nonlimiting example of a first sensing element may be an electrode pair coated with a sensing material and positioned on a substrate. The impedance analyzer may measure the gas response of this first sensing element at frequencies or at a single frequency in the vicinity of the dielectric relaxation peak of the sensing material. A nonlimiting example of a second sensing element may be a mechanical resonator such as a tuning fork resonator, a thickness shear mode resonator, or a surface acoustic wave resonator, coated with a sensing material. The impedance analyzer may measure the resonant peak frequency position of this resonant second sensing element.

The multi-gas sensing system 100 may include the system controller 120. The system controller 120 may include one or more devices such as, but not limited to, a power source 130, a data analytics unit 132, an output device 134 (e.g., such as a safety alarm), and a communication system 136. One or more of the components of the system controller 120 may include one or more processors that include one or more microprocessors, field programmable gate arrays, and/or integrated circuits. In one or more embodiments, the sensing system 100 may be a battery-operated device and/or may be powered using energy available from a main control system or by using harvesting of energy from ambient sources (e.g., light, vibration, heat, electromagnetic energy, or the like). In one or more embodiments, the management circuit 110 and/or the modifier assembly 122 may be a part of the system controller 120. For example, the one or more processors of the system controller 120 may operate in a manner similar to that as the management circuit 110 and/or the modifier assembly 122.

The data analytics unit 132 may be in the form of an integrated circuit controller positioned on the same board as the sensing elements. As one example, the system 100 may operate with a power demand of about 30 milliamp hour per hour of substantially continuous operation or less. The data analytics unit 132 may receive data from one or more sensing elements 102A-C directly or via the management circuit 110, from other sensing elements such as temperature and/or ambient humidity sensing elements positioned on the same board. The data analytics unit 132 may receive data wirelessly from one or more sensing elements 102A-C directly or via the management circuit 110, or from other sensing elements positioned at different locations in or around the system 100, or the like.

The data may be stored in short term and/or long term memory storage devices, such as archiving communication systems, which may be located within or remote from the system 100 and/or reconstructed and displayed for an operator, such as at an operator workstation, displayed via an output device of the system 100, or the like. The data analytics unit 132 may include one or more processors for analyzing the data received from the management circuit 110. For example, the one or more processors may be one or more computer processors, controllers (e.g., microcontrollers), or other logic-based devices that perform operations based on one or more sets of instructions (e.g., software). The instructions on which the one or more processors operate may be stored on a tangible and non-transitory computer readable storage medium, such as a memory device. The memory device may include a hard drive, a flash drive, RAM, ROM, EEPROM, and/or the like. Alternatively, one or more of the sets of instructions that direct operations of the one or more processors may be hard-wired into the logic of the one or more processors, such as by being hard-wired logic formed and/or stored in the hardware of the one or more processors.

Figure 2:
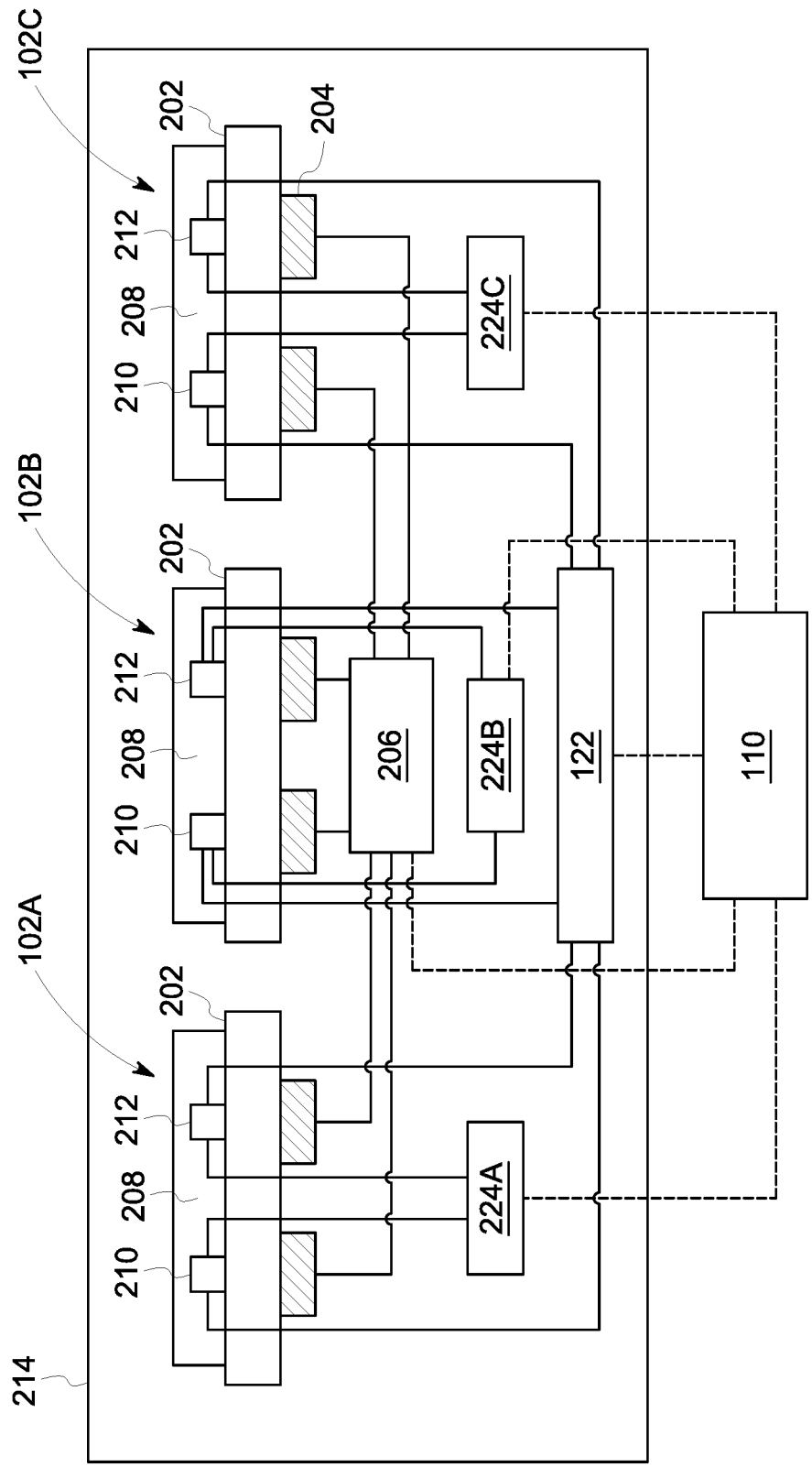
FIG. 2 illustrates a sensing circuit of the multi-gas sensing system shown in FIG. 1.

FIG. 2 illustrates one embodiment of the sensing circuit 200 of the multi-gas sensing system 100. The sensing circuit 200 includes one or more sensing elements 102A-C. Each of the sensing elements 102A-C may be operationally in contact with a fluid that may contain one or more analyte gases therein. The sensing elements 102A-C include a common substrate 202, such as a dielectric material. Suitable materials of the substrate 202 may include silicon dioxide, silicon nitride, alumina, ceramics, and others. Each sensing element 102A-C also includes a sensing film or sensing material 208 that is coupled to the substrate 202, and electrodes 210, 212. Suitable examples of sensing materials or sensing films include a metal oxide material, a composite material, semiconducting materials, n-type semiconducting materials, p-type semiconducting materials, a combination of n-type and p-type semiconducting materials, nanocomposite materials, inorganic materials, organic materials, polymeric materials, formulated materials, any known sensing material, or the like. Suitable electrodes may be formed using metal etching, screen-printing, ink-jet-printing, and mask-based metal deposition techniques. The thickness of fabricated electrodes on the substrates may be in the range from about 10 nanometers to about 1000 micrometers. The materials for the interdigital electrode structures, substrate, sensing layer, and electrode formation methods may be selected based at least in part on the application specific parameters.

The sensing material 208 is exposed to, in contact with, in indirect contact with, or the like, at least one analyte gas. One or several heating elements 204, such as high resistance bodies, are coupled to a different side of the substrate 202 relative to the sensing material 208. The heating elements 204 receive electric current from a heater controller 206, which represents hardware circuitry that conducts the heater current or voltage to the heating elements 204 to heat the substrate 202 and to heat the sensing film or sensing material 208 that is coupled to another side of the substrate 202. For example, in one or more embodiments of the inventive subject matter described herein, the sensing material 208 utilizes a metal oxide sensing film. The management circuit 110 may manage a temperature of each of the sensing elements 102 by controlling operation of the heater controller 206 to control each of the heating elements 204. The sensing material 208 can include one or more materials deposited onto the substrate 202 to perform a function of predictably and reproducibly affecting the impedance sensor response upon interaction with the environment. For example, a metal oxide, such as $SnO_2$ or any other material may be deposited as the sensing material 208.

In one or more embodiments, one or more filters may be disposed over one or more of the sensing elements 102. For example, the one or more filters may be a barrier or alternative protection mechanism or device that may prohibit or reduce an amount of gaseous, liquid, and/or solid particles may be in contact with the sensing material 208, the electrodes 210, 212, or the like. As one example, a single filter may be disposed over one or more elements, or alternatively individual sensing elements may include individual filters disposed over the top of the individual sensing elements. The one or more filters may be a gas-permeable membrane filter such that the filter may enable gases of interest to pass through the filter from one side to another, and may prohibit or reduce an amount of interferent gases or solid particles that may pass through the filter from one side to another. In one or more embodiments, the gas-permeable membrane filter may include a fluoropolymer or a fluoropolymer coating. Optionally, the filter may include an alternative coating such as a flame retardant.

The sensing electrodes 210, 212 of each sensing element 102 are coupled with and/or disposed in the sensing material 208 and are connected with the substrate 202 in the illustrated embodiment. The sensing electrodes 210, 212 are conductive bodies that are conductively coupled with one or more of the modifier assembly 122, transducers 224A-C, and a management circuit 110. In one or more embodiments, the transducers 224A-C are electrode structures that are connected to an impedance detector system, and a sensor is a transducer that is coated with a sensing material. The management circuit 110 may include an impedance detector system or a resistance detector system. Each of the modifier assembly 122, the transducers 224A-C, and the management circuit 110 may have one or more processors that include one or more microprocessors, field programmable gate arrays, and/or integrated circuits.

In the illustrated embodiment of FIG. 2, each sensing element 102A-C is operationally coupled with transducers 224A-C, respectively. Alternatively, the sensing circuit 200 may include a single transducer that is conductively coupled with each sensing element 102 that may receive the electrical responses from each sensing element 102 and convert variations of the electrical responses into a physical quantity.

In one or more embodiments, the sensing electrodes 210, 212 may be coated with a sensing material that is responsive to one or more analyte gases of interest. The one or more processors of the management circuit 110 may direct the sensing electrodes 210, 212 to apply the electrical stimuli at one frequency, such as an electrical excitation frequency or a single excitation frequency. For example, the management circuit 110 may excite the sensing elements 102 with an alternating current at at least one predetermined frequency, at a predetermined frequency range, or the like.

The one or more processors of the management circuit 110 may receive an electrical signal from the sensing electrodes 210, 212 of each sensing element 102 that represents the electrical impedance or impedance response of the sensing elements 102 during exposure of the sensing material 208 to the fluid sample. For example, the one or more processors of the management circuit 110 may measure the one or more electrical responses of the sensing elements 102 responsive to exciting the electrodes 210, 212 with the alternating electrical current at the at least one frequency or the frequency range.

The management circuit 110 may determine one or more characteristics of the sensing circuit 200 based on the electrical responses from each of the different sensing elements 102. The characteristics of the sensing circuit 200 may include a temperature of one or more of the sensing elements, a temperature variance between two or more sensing elements, a state of the sensing circuit 200 based on a configuration of the sensing elements 102, one or more ambient conditions (e.g., ambient temperature, humidity, or the like) within a predetermined area that is proximate the sensing circuit 200, or the like. In one or more embodiments, the management circuit 110 may manage a configuration of each of the one or more sensing elements, such that the management circuit 110 may manage the resistor-capacitor configuration of at least one of the sensing elements. The management circuit 110 may determine the state of the sensing circuit 200 based on the resistor-capacitor configuration of each of the sensing elements of the sensing circuit. Optionally, the state of the sensing circuit 200 may be based on another configuration of the sensing circuit.

In one or more embodiments, the management circuit 110 may be referred to as a frequency impedance source and detector system. The management circuit 110 examines the electrical impedance of the sensing elements 102 in order to determine the presence and/or amount (e.g., concentration) of one or more analyte gases in the environment to which the sensing material 208 of each sensing element 102 is exposed, as described herein. The management circuit 110 may provide scanning capability to measure sensor impedance responses at a single or at plural discrete frequencies. Alternatively, the system controller 120 may provide capability to measure sensor impedance responses across a frequency range.

The sensing circuit 200 may be operably coupled with the modifier assembly 122 that may include a multiplexer. The multiplexer may be a single multi-frequency scanning signal analyzer that may operate with a power demand that is less than 10 milliwatts (mW), less than 5 mW, or in a more preferred embodiment, less than 1 mW. In one or more embodiments, each of the sensing elements 102A-C may be conductively coupled with the modifier assembly 122. The system controller 120 and/or the management circuit 110 may direct one or more of the sensing elements 102 to change the impedance of the electrical stimuli applied to the corresponding sensing material 208 without changing the excitation frequency. As one example, the modifier assembly 122 may include a bank of circuits having plural circuits (not shown) to change the impedance of each of the sensing elements 102 based on which circuits are electrically coupled with or electrically disconnected from the management circuit. Optionally, the modifier assembly 122 may include a single circuit that may be a variable circuit or variable device that may change the impedance of each of the sensing elements 102. In alternative embodiments, the modifier assembly may include a multiplexer having any alternative configuration, one or more circuits, or any combination therein.

The management circuit 110 and/or the system controller 120 may control the modifier assembly 122 to apply the electrical stimuli to each of the sensing elements 102 at single or discrete impedances, or at predetermined ranges of varying impedance, for interrogation of the sensing material 208 of each respective sensing element 102 and at what interrogation time to apply to measure the sensor response at each frequency. For example, the multiplexer of the modifier assembly may electrically connect and/or electrically disconnect one or more of the different sensing elements 102 with the management circuit 110 and the corresponding sensing electrodes 210, 212 to change which sensing elements 102 of the sensing circuit 200 are electrically coupled with and electrically disconnected from the modifier assembly 122 and the management circuit 110. For example, the modifier assembly 122 may change the impedance of each of the sensing elements 102 without changing the electrical excitation frequency of the electrical stimuli applied to the sensing electrodes 210, 212.

The multiplexer of the modifier assembly 122 may combine the plural electrical response signals received from each of the sensing elements 102 into a single output that is directed to the management circuit 110. The management circuit 110 receives the electrical response signals responsive to exciting the electrodes 210, 212 at the alternating current at at least one predetermined frequency and determines the one or more characteristics of the sensing circuit 200. The management circuit 110 may transmit, or otherwise communicate, the electrical response signals and the determined characteristics of the sensing circuit 200 to the one or more processors of the system controller 120. A concentration of at least one gas analyte may be determined based on the electrical responses of the sensing elements 102 and the characteristics of the sensing circuit 200. For example, the data analytics unit 132 of the system controller 120 may convert rase sensor responses into the analytically useful concentrations of detected gases, and when necessary, activate a safety alarm. Additionally, the data analytics unit 132 may determine a concentration of at least one gas analyte based on one or more temperatures of each of the sensing elements, the ambient conditions proximate the sensing circuit 200 (e.g., within a predetermined proximity or area of the sensing circuit, such as within 1 meter, 5 meters, 10 meters, 100 meters, or the like), or the like.

As one example, the system controller 120 may determine the concentration of at least one analyte gas based on electrical responses from two or more different sensing elements (e.g., sensing elements 102A, 102B). The first sensing element 102A may be operated at a first substantially constant temperature and the second sensing element 102B may be operated at a different, second substantially constant temperature. For example, the management circuit 110 may control the heating elements 204 such that the first sensing element 102A may operate at a first temperature, and that the second sensing element 102B may operate at a different temperature that may be greater than or less than the first temperature.

As another example, the system controller 120 may determine the concentration of the one or more gas analytes based on electrical responses from two or more different sensing elements, such as sensing elements 102A and 102B. The management circuit 110 may control operation of the heating elements 204 to operate the first sensing element 102A at periodically variable temperatures and may operate the second sensing element 102B at different periodically variable temperatures. For example, the heating elements 204 may change a temperature of the first sensing element 102A (e.g., such as within a temperature range) that increases and/or decreases the temperature to predetermined values at predetermined times, for predetermined durations, or any combination therein. Additionally, the heating elements 204 may change a temperature of the second sensing element 102B (e.g., within a different or the same temperature range), that increases and/or decreases the temperature to different predetermined values at different predetermined times, for different predetermined durations, or any combination therein. Optionally, the first and second sensing elements 102A, 102B may operate a similar temperature ranges for different durations, may operate at similar durations but at different temperature ranges, may operate at similar temperatures and durations but at different times, or the like.

The sensing elements 102A-C including the sensing material 208 and substrate 202, the heating elements 204, the heater controller 206, the modifier assembly 122, and the transducers 224A-C disposed within a common housing 214. The housing 214 may be operably coupled with the substrate or circuit board 104 of the system 100. Optionally, one or more sensing elements 102 may be disposed in individual housings to separate each sensing element from each other sensing element. Optionally, one or more of the modifier assembly 122, the heater controller 206, one or more of the transducers 224, or the management circuit 110 may be operably coupled with the circuit board 104 of the system 100 and may be disposed outside of or separate from the common housing 214. Optionally, one or more of the components of the system 100 may be disposed or contained within housings together with or separate from any other components of the system 100.

Figure 4:
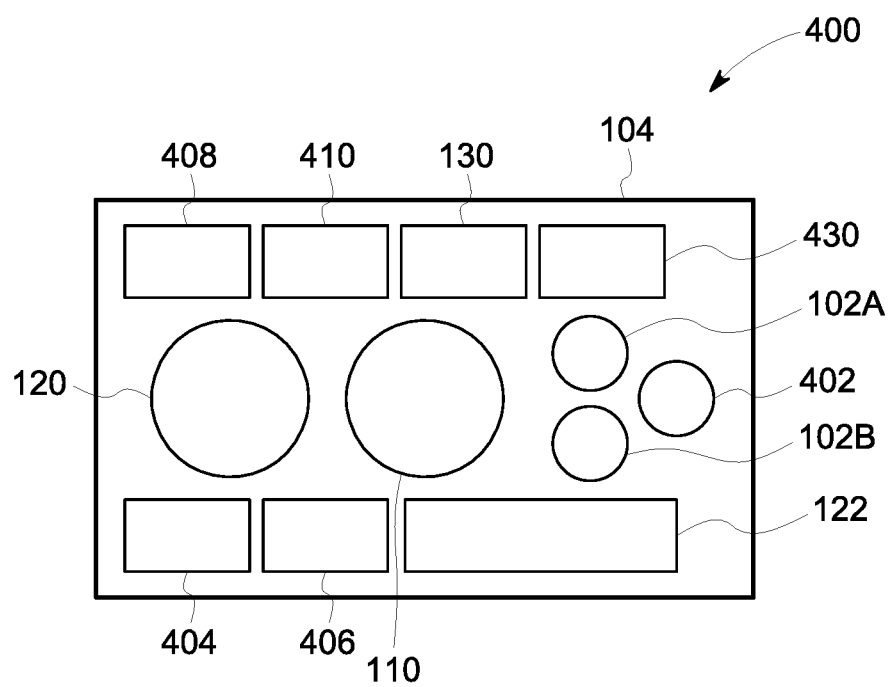
FIG. 4 illustrates a system layout of a multi-gas sensing system in accordance with one embodiment.

FIG. 4 illustrates a system layout of a multi-gas sensing system 400 in accordance with one embodiment. The components and devices of the system 400 are disposed on the substrate or circuit board 104. In one or more embodiments, one or more of the components or devices of the system 400 may be disposed on one or both sides of the board 104. The system 400 may include one or more power devices or components such as the power source 130 or power switch, a power regulator 430, a nonvolatile memory or other memory or storage device 406, a charging source 408, such as a micro-USB or the like, or a charger or charging device 410. In one or more embodiments, the power source 130 may be or include a battery source, or any alternative untethered power source. The system 400 may include processing components such as the management circuit 110, the system controller 120, and the modifier assembly 122. The management circuit 110 may include one or more processors that include one or more microprocessors, field programmable gate arrays, and/or integrated circuits that may operate or function as an impedance analyzer, a resistor detector system, or the like. The system controller 120 may include one or more processors that may operate as a data analytics unit, a memory system (e.g., memory 406), or the like. The modifier assembly 122 is illustrated as separate from the system controller 120 and the management circuit 110, but alternatively may be included with one or both of the management circuit 110 or the system controller 120.

The system 400 includes two different sensing elements 102A, 102B. In one or more embodiments, the sensing elements 102A, 102B may each be designed to sense or otherwise detect the presence of one or more of methane (CH4), carbon monoxide (CO), or the like. Optionally, the different sensing elements may be designed to sense or otherwise detect different gases. The system 400 includes a sensing element 402 that may be designed to sense or otherwise detect ambient conditions, such as ambient temperature, ambient humidity, ambient pressure, or the like. For example, the sensing elements 102A, 102B may communicate electrical responses to the management circuit 110 responsive to the management circuit exciting the sensing elements 102A, 102B with the alternating current at the at least one predetermined frequency. The management circuit 110 may measure the electrical responses from the sensing elements 102A, 102B to determine one or more characteristics of the sensing circuit. Additionally, the sensing element 402 may detect ambient conditions of an area proximate the system 100, and the management circuit 110 may determine characteristics of the system 100 based on the ambient conditions detected by the sensing element 402. The one or more processors of the system controller 120 may receive the electrical responses and the characteristics of the sensing circuit and determine a concentration of at least one gas analyte, such as a gas analyte of interest, based on the electrical responses and the characteristics of the sensing circuit.

In one or more embodiments, the system 400 may include an output device 404. As one example, the output device may be illustrated as LED lights. For example, the LED lights may illuminate based on the electrical responses of the sensing elements, based on characteristics of the of the sensing circuit, or the like. Optionally, the output device 404 may be any alternative safety device that may illuminate, sound an alarm, vibrate, or otherwise communicate to an operator of the system 100 if the system controller 120 determines that a gas of interest exceeds a predetermined threshold. For example, the output device 404 may notify the operator if the operator is in within an area that is deemed unsafe, is in the presence of an unsafe concentration of a particular gas, or the like. In one or more embodiments, the output device 404 may output a sound or visual notification that may vary based on the amount of concentration of the analyte gas. For example, as the concentration of the gas increases, the output device 404 may flash a light or sound an alarm at an increased frequency, and alternatively, as the concentration decreases, the output device 404 may flash a light or sound an alarm at a decreased frequency. Optionally, the tone or pitch of the alarm may change or the color of the light may change based on the determined concentration of the analyte gas, based on the processors determining the presence of a particular gas instead of another gas or other gases, or the like. Optionally, the output device 404 may otherwise notify the operator of for any alternative reason, at any alternative time, and in any alternative manner.

Figure 5:
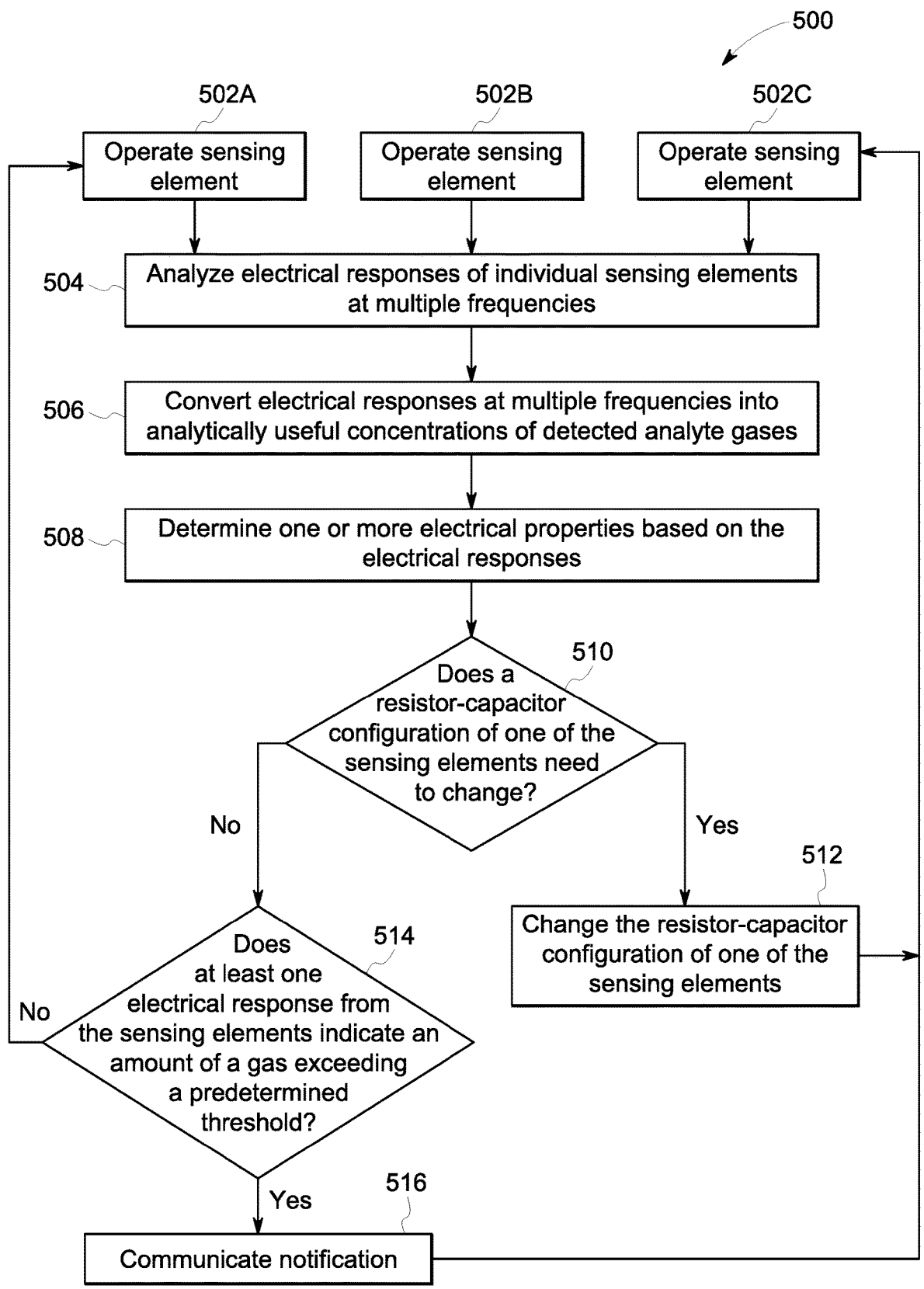
FIG. 5 illustrates a flowchart of one embodiment of a method for sensing multiple different gas analytes using the multi-gas sensing system in accordance with one embodiment.

FIG. 5 illustrates a flowchart 500 of one embodiments of a method for sensing multiple different gas analytes using a multi-gas sensing system in accordance with one embodiment. The multi-gas sensing system may be the system illustrated in FIG. 1. At 502A-C, each of the sensing elements 102A-C may be operated. For example, the management circuit may excite each of the sensing elements with an alternating current at at least one predetermined frequency. The management circuit may excite sensing element 102A at a first predetermined frequency, and may excite the sensing elements 102B, 102C at different, unique or common frequencies relative to each other and the sensing element 102A. Optionally, one or more of the sensing elements 102A-C may be excited at a predetermined frequency range. In the illustrated embodiment of FIGS. 1 and 2, the system includes three sensing elements. Alternatively, the system may include less than three or more than three sensing elements. Alternatively, the system may include only one sensing element.

In one or more embodiments, the management circuit may manage a temperature of one or more of the sensing elements by controlling a heating element. For example, the management circuit may control operation of the heating element such that one or more of the sensing elements are operated at a predetermined temperature, are operated at a predetermined temperature range, such that the different sensing elements are operated at different temperatures or at a range of different temperatures, or the like. In one embodiment, the management circuit may control the heating element to periodically change the temperature of the first sensing element 102A and to substantially maintain a temperature of the second and third sensing elements 102B, 102C. For example, the management circuit may control the heating element such that the first sensing element 102A is operated at a first constant or first variable temperature, and the second sensing element 102B is operated at a different, second constant temperature or second variable temperature. As another example, the management circuit may control the heating element such that the first sensing element 102A is operated at periodically variable temperatures, and the second sensing element 102B is operated at different periodically variable temperatures. The different periodically temperatures of the second sensing element may be substantially the same temperatures, but heated at different periodic times than the first sensing element. Alternatively, the first and second sensing elements may be heated at substantially the same or common periodic times, but the first sensing element may be heated to temperatures that are different than the temperatures of the second sensing element.

The management circuit may synchronize the temperature of one or more sensing elements with the excitation of the one or more sensing elements. For example, the management circuit may synchronize controlling the heating elements to control a temperature of one or more sensing element to a predetermined at substantially the same time, or within a predetermined time window, as exciting the one or more sensing elements at the alternating current of the predetermined frequency. For example, the management circuit may control the heating elements and excite the one or more sensing elements at substantially the same time, within a time window, or the like. Optionally, the management circuit may synchronize changing a temperature of the one or more sensing elements with a duration of excitation of the sensing elements. Optionally, the management circuit may synchronize substantially maintaining a temperature range of the one or more sensing elements while variably exciting the sensing elements at the predetermined frequency or frequency range. Optionally, the management circuit may otherwise synchronize the temperature of the sensing elements with the excitation of the sensing elements in any alternative configuration or based on one or more predetermined rules.

At 504, the one or more processors of the management circuit and/or the system controller may analyze the electrical responses from the sensing elements responsive to the excitation of the sensing electrodes of the sensing elements. The electrical responses may be represented as signal outputs from each of the one or more sensing elements. An alternating electrical current may be applied to each of the one or more sensing elements at one or more different frequencies, or at one or more different resistor-capacitor configurations of each of the sensing elements. For example, the first sensing element may have a first resistor-capacitor configuration, and a first frequency may be applied to the sensing electrodes of the first sensing element to excite the first sensing element. Alternatively, the second sensing element may have a second, different resistor-capacitor configuration, and a different, second frequency may be applied to the sensing electrodes of the second sensing element. Alternatively, one or more of the sensing elements may have common resistor-capacitor configurations, or a common frequency may be applied to excite one or more of the sensing elements.

Figure 6:
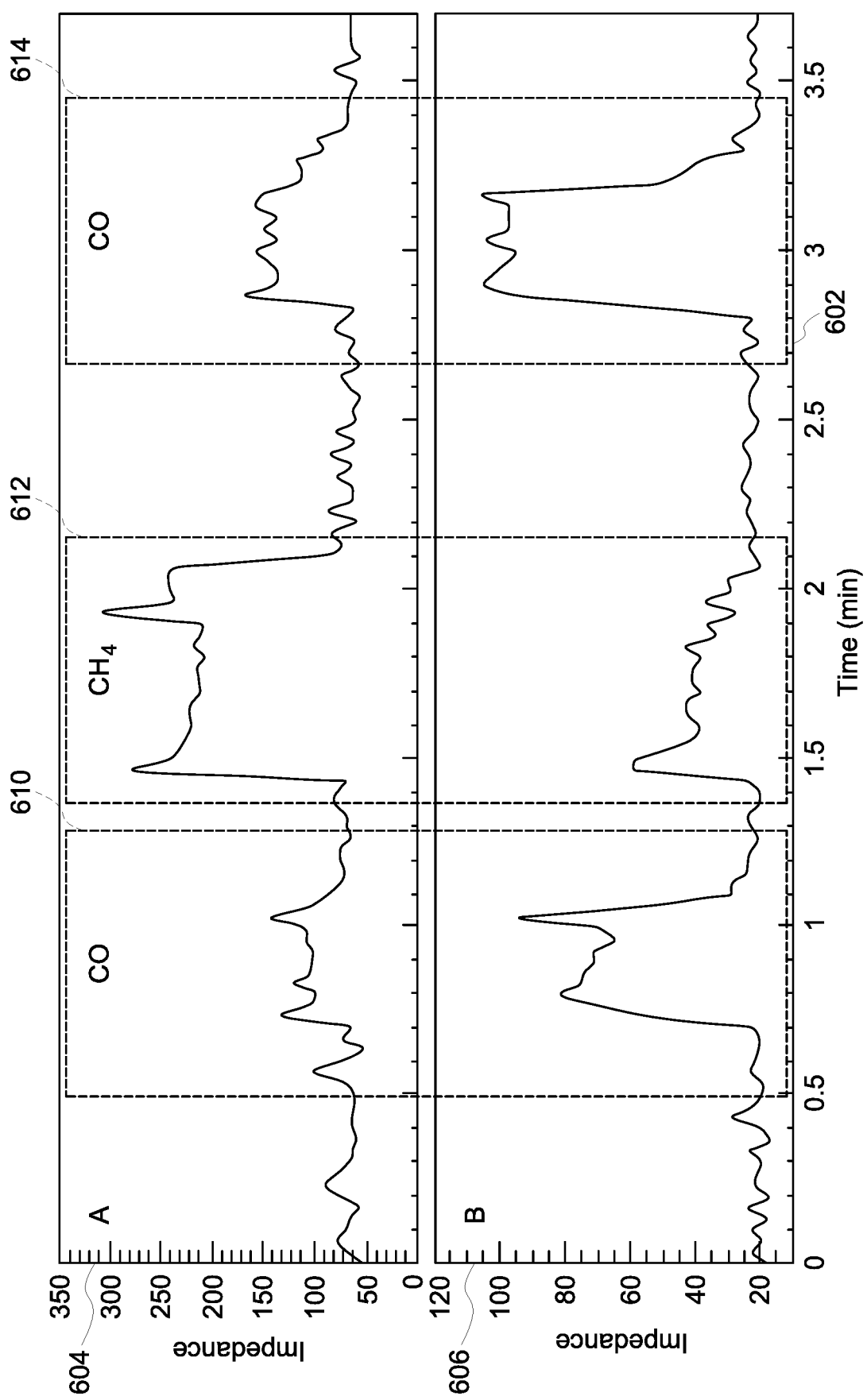
FIG. 6 illustrates graphical illustrations of electrical responses of individual sensing elements of a multi-gas sensing system in accordance with one embodiment.

FIG. 6 illustrates graphical illustrations of electrical responses of individual sensing elements of a multi-gas sensing system in accordance with one embodiment. Graph A represents the electrical responses from a first sensing element that may be designed to detect the presence of methane (CH4). Graph B represents the electrical responses from a second sensing element that may be designed to detect the presence of carbon monoxide (CO). Alternatively, the electrical responses may be received from a single sensing element that may be configured to operate to detect the presence of CH4, CO, and any other gas. Graphs A and B are illustrated having a common horizontal axis 602 representative of time, and vertical axes 604, 606, respectively, representative of the impedance of the sensing circuit 200.

Measurements of one or more of the real Z' or imaginary Z" parts of the impedance of the sensing circuit 200 may be performed within a dielectric relaxation region of the sensing circuit 200. The dielectric relaxation region of the sensing system 100 may be a range of frequencies within a designated threshold of the measured impedance of the sensing circuit 200 at the occurrence of relaxation peak and/or a relaxation point frequency or an inflection point frequency range of the imaginary Z" part of the impedance. For example, the relaxation peak (also known as relaxation frequency) may be identified as the location along the imaginary part of an impedance spectra at which the impedance response changes from being concave to convex, or changes from being convex to concave. The inflection point frequency is the frequency or the frequency range at which the inflection point occurs. Alternatively, the inflection point can be determined be examining the real part of the measured impedance of the sensing material 208 to locate where the curvature of the real part of the impedance changes from a concave shape to a convex shape, or from a convex shape to a concave shape. In one or more embodiments, the electrical response of the sensing system is monitored at the gas-modulated front shoulder of the dielectric relaxation peak of the semiconducting sensing material. For an n-type semiconducting sensing material, the front-edge shoulder may be the high-frequency region of the relaxation peak. For a p-type semiconducting sensing material, the front-edge shoulder may be the low-frequency region of the relaxation peak.

As one example, the sensing circuit may be exposed to about 1.36% volume of CH4 and 1090 parts per million (ppm) of CO. As illustrated in Graphs A and B, the second sensing element (e.g., the CO sensor) detects an increase in the impedance in the presence of CO as illustrated in a first section 610, but the first sensing element (e.g., the CH4 sensor) indicates only a minimal increase in impedance in the presence of CO. Similarly, the second sensing element detects an increase in the presence of CO as illustrated in a third section 614, but the first sensing element has only a minimal increase. Alternatively, the first sensing element detects an increase in impedance in the presence of CH4 as illustrated in a second section 612, but the second sensing element has only a minimal increase. Graphs A and B illustrate discrimination between the CH4 and CO by the first and second sensing elements of the sensing circuit.

Returning to FIG. 5, at 506, the electrical responses at multiple frequencies received from one or more sensing elements are converted into analytically useful concentrations of detected analyte gases. For example, the management circuit and/or the data analytics unit of the system 100 may perform analysis on the electrical responses received from the sensing elements to determine one or more concentrations of the one or more sensed analyte gases. The analysis may be based on one or more of the electrical responses of the sensing elements; characteristics of the sensing circuit such as, but not limited to, temperatures of the sensing elements, states of the sensing circuit based on configurations of the sensing elements, ambient conditions proximate the sensing circuit, or the like; or any combination of two or more therein. In one or more embodiments, the analysis may be based on one or more of the sensing elements being operated at periodically variable temperatures, one or more sensing elements being operated at common or unique substantially constant temperatures, different discrete frequencies or frequency ranges used to excite the sensing elements, or the like.

Figure 7:
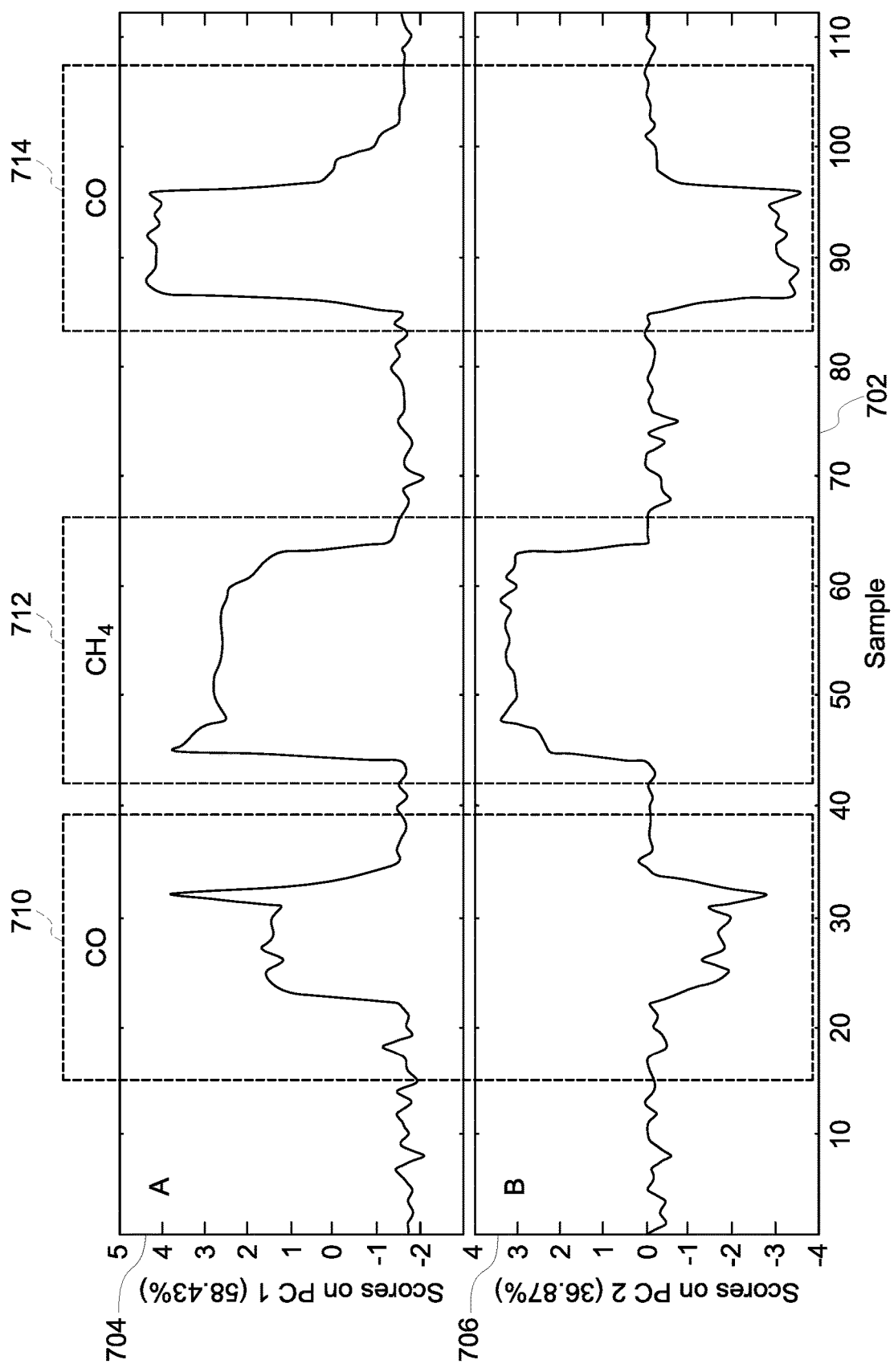
FIG. 7 illustrates graphical illustrations of electrical responses of analyzed electrical responses of the individual sensing elements of the multi-gas sensing system shown in FIG. 6.

For example, FIG. 7 illustrates graphical illustrations of the results of analyzed data of electrical responses of two sensing elements of the multi-gas sensing system shown in FIG. 6.

The electrical responses may be evaluated using one or more different statistical analysis tools, such as, for example, by performing Principal Component Analysis (PCA) on the electrical responses and other characteristics obtained by the system controller. Optionally, the concentration of one or more gases may be computed from a multivariable transfer function that may be built based on the electrical responses to the alternating electric current of the management system, temperatures of the sensing elements, states of the resistor-capacitor configurations of the sensing elements, information about environmental conditions around the multi-gas sensing system from the sensing circuit or other sensors, or the like. Optionally, alternative statistical analysis may be used to evaluate the data obtained by the system controller.

Graph A represents the results of analyzed data of the combined electrical responses using PCA and presented as the scores of the Principal Component #1 as a function of experimental time.

Graph B represents the results of analyzed data of the combined electrical responses using PCA and presented as the scores of the Principle Component #2 as a function of experimental time.

Graphs A and B are illustrated having a common horizontal axis 702 representative of experimental time, and vertical axes 704, 706, respectively, representative of a linear scale of Principal Component #1 and Principal Component #2, respectively, of the developed PCA classification.

As illustrated in Graph A, first and third sections 710, 714, indicate the increased concentrations of CO, and a second section 712 indicates the increased concentration of CH4. For example, the first and third sections indicate the PCA Principal Component #1 responses to CO gas (e.g., sections 610, 614 of Graph B) of FIG. 6, and the second section indicates the PCA Principal Component #1 response to CH4 gas (e.g., section 612 of Graph A) of FIG. 6.

As illustrated in Graph B, first and third sections 710, 714 indicate the increased concentrations of CO, and a second section 712 indicates the increased concentration of CH4. For example, the first and third sections indicate the PCA Principal Component #2 responses to CO gas (e.g., sections 610, 614 of Graph B) of FIG. 6, and the second section indicates the PCA Principal Component #2 response to CH4 gas (e.g., section 612 of Graph A) of FIG. 6.

In one or more embodiments, the one or more processors of the system controller may provide a baseline correction of the sensing elements. The baseline correction may be done periodically, at scheduled intervals (e.g., after so many minutes, hours, days, years, or the like, of operating), or the like. The baseline correction may also be referred to as calibration of the sensing elements. The amount of correction, or the method of correcting or verifying the baseline, may be based on the electrical responses received from the sensing elements, the temperatures of the sensing elements, the state of the resistor-capacitor configurations of the sensing elements, information about the environmental conditions (e.g., ambient temperature, humidity, pressure, or the like) around or proximate to the multi-gas sensing system, based information received from other sensors or sensing devices, based on information wirelessly communicated to the multi-gas sensing system (e.g., such as from a workstation separate from the multi-gas sensing system), based on information or a protocol stored within the multi-gas sensing system, or the like.

Optionally, the one or more processors may change a selectivity, sensitivity, or linearity of the electrical responses of the multi-gas sensing system 100 to allow the system to be more responsive to one analyte gas versus another analyte gas at different times or under different operating conditions. In one or more embodiments, the one or more processors may dynamically change the selectivity, the sensitivity, or the linearity, such that the one or more processors may change one or more of the selectivity, the sensitivity, or the linearity while the sensing system is operating. Optionally, the one or more processors may change one or more of the selectivity, the sensitivity, or the linearity of the electrical responses of the sensing system when the system is not sensing. For example, the one or more processors may determine a relaxation region of an impedance response of the sensing circuit. Both the real part of the impedance and the imaginary part of the impedance have a relaxation region. As one example, this relaxation region can be determined by examining the real part of the measured impedance of the sensing material 208 as a function of frequency to locate where the real part of the impedance changes from high impedance value with substantially zero slope at low frequencies, to decreasing impedance values with a relatively high slope at higher frequencies, and to decreasing impedance values with a relatively low slope at even higher frequencies, and where impedance values are approaching zero at the highest frequencies.

The one or more processors may determine a position of the relaxation peak of the relaxation region of the imaginary part of the sensor impedance by identifying the inflection point frequency of the sensing circuit 200. The inflection point frequency can be determined as the frequency of the electric current associated with the inflection point.

The one or more processors may determine frequency ranges of sensor operation that are lower and higher than the relaxation peak of the imaginary part of the sensor impedance and that are at or about (e.g., within 1%, within 3%, within 5%, or within 10% in different embodiments) the relaxation peak of the imaginary part of the sensor impedance. An electric current may be applied to the sensing material 208 via the electrodes 210, 212 of one or more sensing elements only at frequencies that are greater than the inflection point frequency and/or that are within the range of frequencies that are greater than the inflection point frequency. Operating the sensing circuit 200 at these frequencies can improve the selective sensing of the sensing circuit 200 (e.g., the sensitivity of the sensing circuit 200) to one or more analytes of interest in the second sample relative to one or more other analytes (and relative to operating the sensing circuit 200 at a frequency or frequencies that are at or below the inflection point frequency). The sensitivity of the sensing circuit 200 includes a measured sensor response signal per analyte concentration unit.

As another example, the one or more processors may selectivity sense at least one analyte of interest with improved suppressed effects of interferences. Resistance and capacitance properties of the sensing circuit 200 are measured during exposure of the sensing circuit 200 to a first gas sample and are measured during exposure of the sensing circuit 200 to a second gas sample. The one or more processors determine a capacitance value or a range of capacitance values of one or more passive electrical components (e.g., capacitive elements) in order to change a capacitance of one or more sensing elements of the sensing circuit 200 to match a frequency range or a discrete frequency response of the system controller within a dielectric relaxation region of the sensing circuit 200. Changing the capacitance of the sensing circuit 200, that is coupled with the system controller, allows the system controller to selectively sense an analyte of interest (e.g., methane, ethane, another hydrocarbon, hydrogen, carbon monoxide, or the like) with suppressed effects of interferences.

Selective sensing of one or more analytes of interest is performed using the sensing circuit 200 operating within a dielectric relaxation region of the sensing circuit in order to match a discrete frequency response or a frequency response range of the system controller 120. For example, the sensing material 208 of each sensing element of the sensing circuit 200 can be exposed to a gas sample potentially having one or more analytes of interest therein. The system controller 120 can communicate a control signal to the management circuit 110 to direct the management circuit 110 to apply alternating electric current to the sensing material 208 via the electrodes 210, 212 either over a designated frequency response range or at the designated discrete frequency of the system controller 120 that is within the dielectric relaxation region of the sensing circuit 200. Operating the sensing circuit 200 at these frequencies can increase the selective sensing of the multi-gas sensing system 100 (e.g., the sensitivity of sensing of the sensing system 100) to one or more analytes of interest in the sample relative to one or more other analytes (and relative to operating the sensing circuit 200 at a different frequency or different frequency range of the system controller 120). The sensitivity of the sensing circuit 200 includes a measured sensor response signal per analyte concentration unit.

Returning to FIG. 5, a determination is made if a resistor-capacitor configuration of one of the sensing elements needs to change. If the configuration does need to change, flow of the method proceeds towards 512, where the management circuit changes the resistor-capacitor configuration of one or more sensing elements. Flow of the method returns to 502A-C where the method starts again. Alternatively, if the resistor-capacitor configuration of none of the sensing elements needs to change, flow of the method moves toward 514.

At 514, a determination is made if an amount of at least one gas exceeds a predetermined threshold. For example, the system controller may determine that, based on the analysis performed in steps 504 through 508, that there is an amount of gas present that exceeds a predetermined threshold and the concentration of the gas may be dangerous to the operator or user of the multi-gas sensing system. Optionally, the concentration of the gas may be dangerous for an operator to perform a particular task such as, but not limited to, drive or operate motorized equipment, use inflammatory equipment, remain in the environment without wearing appropriate safety equipment, or the like. In one or more embodiments, a determination may be made if any amount of a particular gas is present. For example, any trace amount, or a minimal amount of a particular gas may be dangerous for the operator to continue operating or to remain in the environment.

In one or more embodiments, the one or more processors of the system controller may determine a responsive action of an asset based on the electrical responses by the multi-gas sensing system. For example, the system controller may determine whether the concentration of at least one gas analyte exceeds a predetermined threshold. If the concentration of the at least one gas analyte does exceed a predetermined threshold, the system controller may determine a responsive action of the asset. Additionally or alternatively, the system controller may a responsive action of a subject responsive to determining that the concentration of the gas analyte exceeds the predetermined threshold. The subject may be a human subject, an animal subject, such as a mammal, a reptile, a bird, a fish, an amphibian, a plant, a robotic subject, or the like. For example, the human subject may be a pilot, a soldier, a firefighter, industrial worker, athlete, traveler, baby or child, hospital patient, disabled person, an elderly person, or the like. In one or more embodiments, the subject may be in operational contact with the asset. The asset may be an industrial asset, such as oil fluid reservoirs, associated piping components, connectors, flow-through components, or the like. Optionally, the asset may be a system such as an airplane, locomotive, truck, passenger car, a home appliance, sport equipment, military system, or the like. The subject may be in operational contact with the asset, and/or the asset may be in operational contact with the subject.

The system controller may determine the responsive action of the asset and/or the subject that is related to results produced by the multi-gas sensing system based on the determined concentration of the at least one gas analyte. The determined concentration of the gas analyte may be based on the electrical responses of the sensing elements, one or more characteristics of the sensing circuit, or the like. Actions that may be taken by the asset may include asset control (e.g., activate a reporting, diagnostics, prognostics, or other outcomes). In one or more embodiments, the system controller may communicate to the subject to take a responsive action, such as by changing a display, sounding an alarm, flashing or blinking a light, changing color of a light, vibrate or change a vibration frequency, or the like. The communication may direct the subject to take one or more actions, such as to move to a different location, to stand up or sit down, to take a medication, to eat and/or drink something, to apply physical activity to move parts of the body of the asset.

If the amount or concentration of the gas analyte does not exceed a predetermined threshold, flow of the method returns to 502 and the method repeats for a predetermined amount of time, while the operator is within the environment, until the operator disables the multi-gas sensing system, or the like. Alternatively, if the amount or concentration of the gas exceeds a predetermined threshold, flow of the method proceeds toward 516. At 516, a notification is communicated to at least the operator of the multi-gas sensing system. For example, the output device (shown in FIG. 4) may be a light that automatically flashes, blinks, or changes to colors to communicate with the operator. Optionally, the output device may be an audio device that beeps, rings, changes pitch or tone, or otherwise communicates with the operator. Optionally, the output device may vibrate, may change frequency of vibrations, may vibrate in a particular pattern, or the like, to communicate with the operator. Optionally, the multi-gas sensing system may communicate with the operator in an alternative manner. In one or more embodiments, the multi-gas sensing system may transmit a wired or wireless communication to another device, such as a workstation or computer, to send notification that an alarm has been triggered based on the concentration of the gas analyte.

Figure 8:
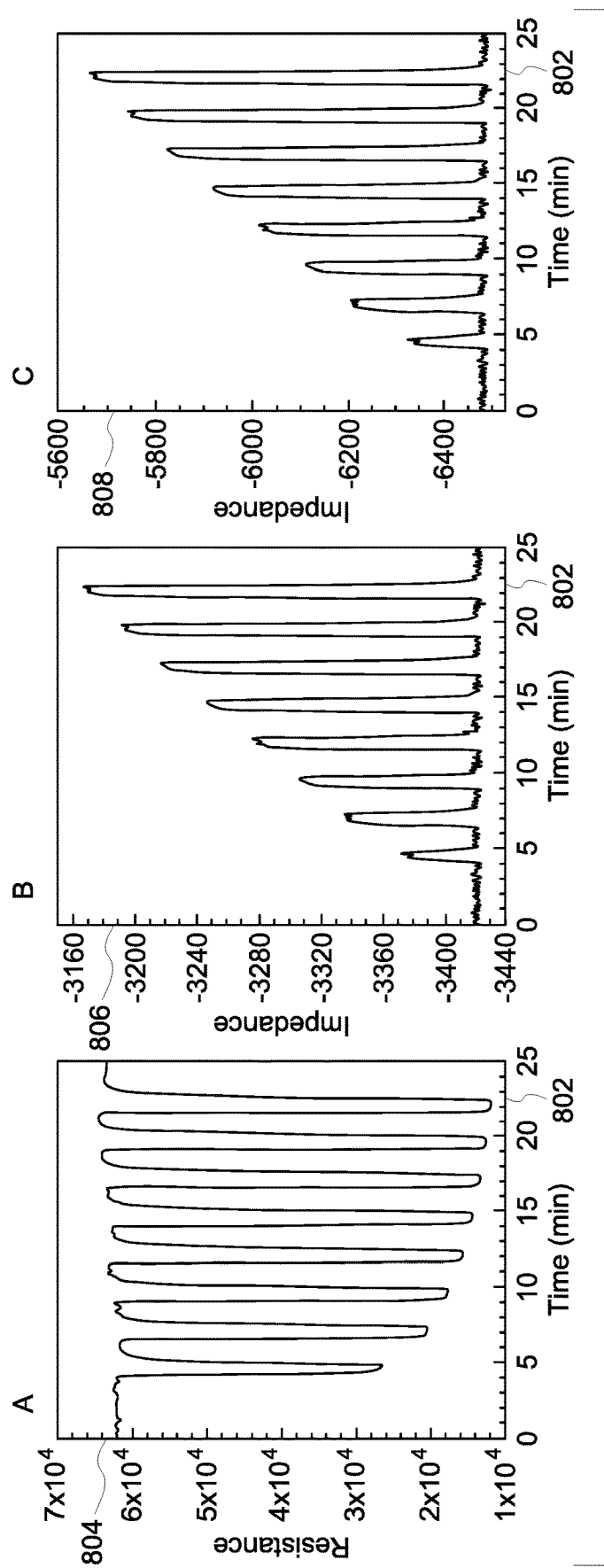
FIG. 8 illustrates graphical illustrations of responses of a metal oxide sensing element to a gas of interest in accordance with one embodiment.

FIG. 8 illustrates graphical illustrations of responses of a metal oxide sensing element to a gas of interest, such as methane, according to one experiment. In the present experiment, the sensing element is a structure with an integrated heater formed on a silicon substrate using MEMS technology and a metal-oxide semiconductor material layer formed on the sensing chip as a surface-mount ceramic package. The sensing element requires a heater power consumption of only about 15 mW. In the present experiment, methane was presented to the sensing element at concentrations of 1087 parts per million (ppm), 2174 ppm, 3261 ppm, 4348 ppm, 5435 ppm, 6522 ppm, 7609 ppm, and 8696 ppm.

Graphs A, B, and C are illustrated having a common horizontal axis 802 representative of experimental time. Graph A is illustrated having a vertical axis 804 representative of resistance, and Graphs B and C are illustrated having vertical axes 806, 808, respectively, representative of impedance. Graph A of FIG. 8 depicts the electrical response of the sensing element as measured by conventional resistance. The resistance response of the sensing element to methane concentrations has a non-linear response. Additionally, the sensitivity decreases with the increase of methane gas concentration. Graphs B and C illustrate the electrical response of the sensing element as measured by the dielectric excitation methodology. Results illustrated in Graph B were achieved by using a desktop impedance analyzer. Results illustrated in Graph C were achieved using an integrated circuit impedance analyzer. The close resemblance of the linearity of the responses and the noise levels in Graphs B and C demonstrate that the quality of sensing of methane using the integrated circuit impedance analyzer was approximately the same when compared to the quality of sensing of methane using the desktop impedance analyzer.

Figure 9:
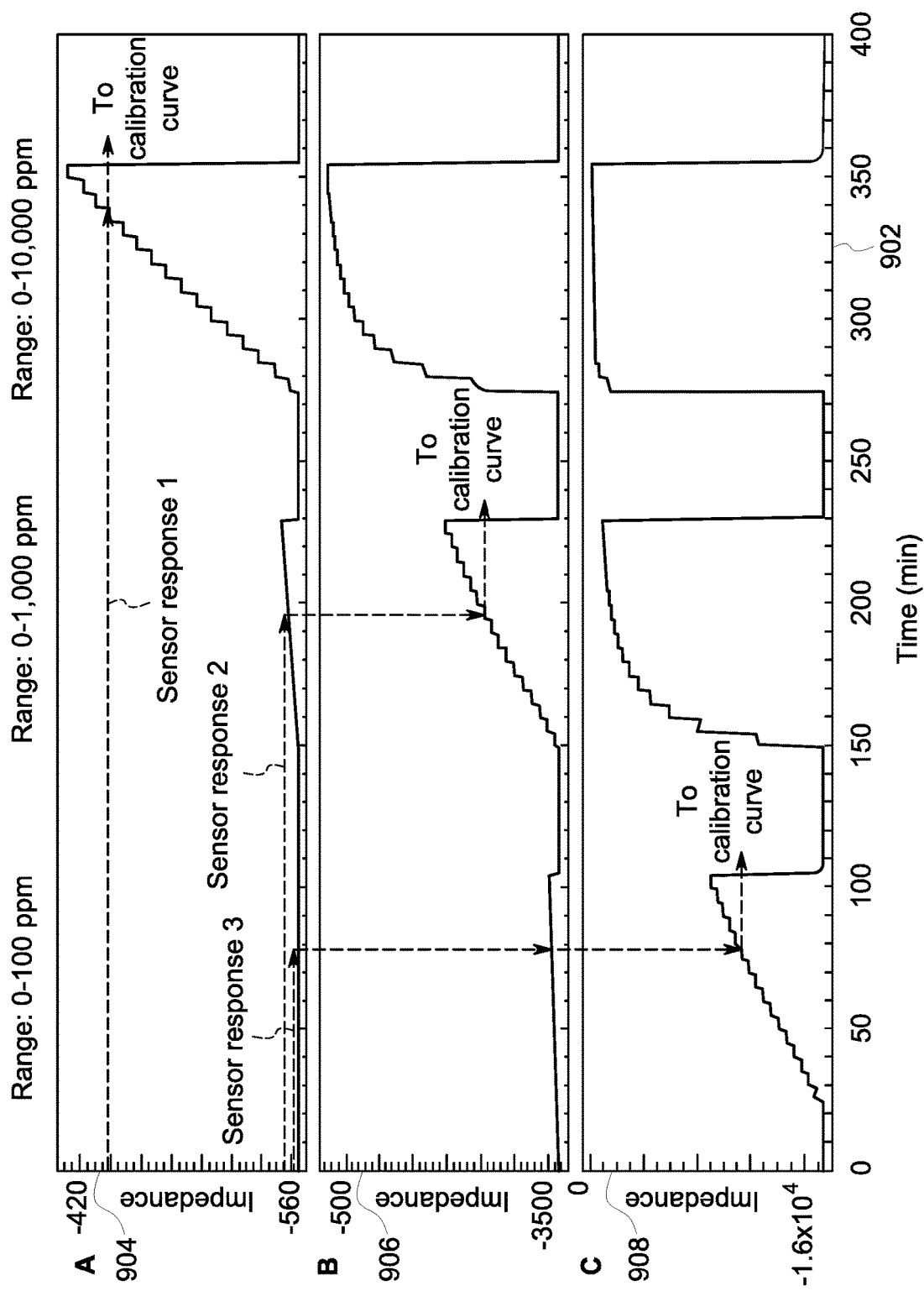
FIG. 9 illustrates graphical illustrations of quantitation of gas concentrations using dielectric excitation gas detection in accordance with one embodiment.

The developed sensor system may measure electrical responses of the sensing element responsive to alternating electrical current applied to the sensing element at one or more different frequencies and/or one or more different resistor-capacitor configurations, of the sensing element. To quantify a gas of interest over its broad range of concentrations with a linear sensor response and its desired resolution, the dielectric excitation methodology can be applied at several frequencies. FIG. 9 illustrates graphical illustrations of three measured sensor responses at three frequencies (Graphs A, B, and C) ranging from relatively high to medium and to relatively low frequency. The Graphs A, B, and C are illustrated having a common horizontal axis 902 representative of experimental time, and vertical axes 904, 906, 908 representative of impedance.

While responses can be measured at all three frequencies of the measurement system, to determine a gas concentration, the calibration curve can be started at the highest frequency. If the sensor response is above the approximately bottom 20% of the sensor responses at this frequency (e.g., sensor response #1), the linear calibration curve at this frequency can be noted and can be related to the gas concentration (Graph A). If the sensor response is below the bottom 20% of the sensor responses at this frequency (e.g., sensor responses #2 and #3), detection can be switched to a decade lower in gas concentrations by using the linear calibration curve at the lower frequency and relating the sensor response to the gas concentration (e.g., sensor response #2, show in Graph B). If the sensor response 3 is below the approximate 10% of the sensor responses at this frequency, detection can be switched further to a decade lower in gas concentrations and the corresponding calibration curve can be utilized (e.g., Graph C). Thus, these sensor responses at different frequencies can allow high-resolution determination of gas concentrations across the broad range of gas concentrations with linear response.

Figure 10:
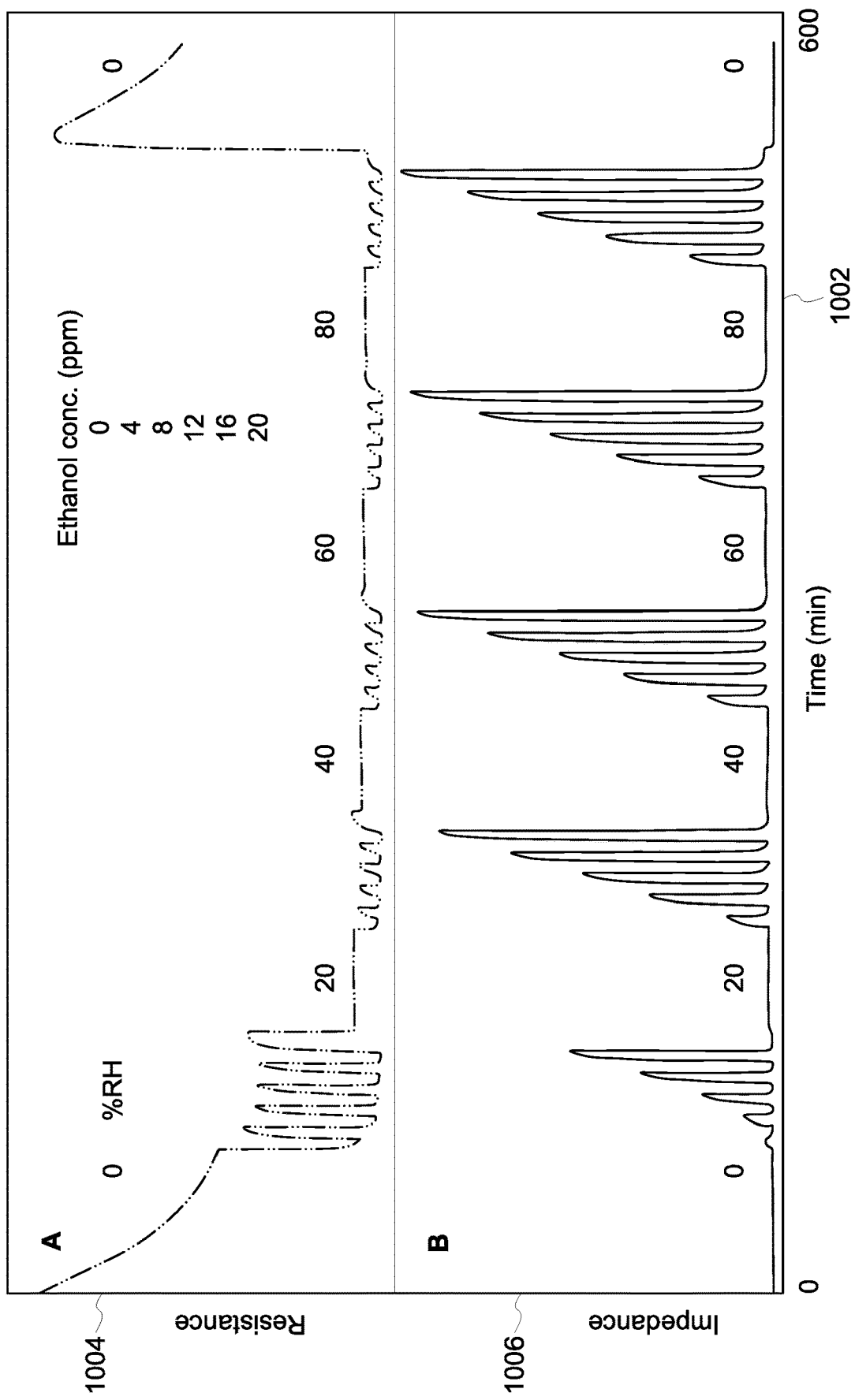
FIG. 10 illustrates effects of water vapor over a range of relative humidity on resistance and dielectric excitation responses.

Another experiment demonstrated that variable humidity of air affects the response of conventional chemiresistor sensors based on metal oxide sensing materials by changing their baseline and gas sensitivity. For example, FIG. 10 illustrates effects of water vapor over a range of 0-80% relative humidity (RH) on resistance and impedance (dielectric response) responses to ethanol (as a model vapor) at concentrations of 4, 8, 12, 16, and 20 ppm. Graphs A and B are illustrated having a common horizontal axis 1002 representative of experimental time. Graph A is illustrated having a vertical axis 1004 representative of resistance, and Graph B is illustrated having a vertical axis 1006 representative of impedance.

The resistance response had a known significant decrease in baseline and decrease in gas sensitivity with the increase of RH (Graph A). Meanwhile, the dielectric excitation and impedance measurement can provide three advancements over resistance measurements (illustrated in Graph B). First, response baseline can be less affected by humidity variations. Second, sensor sensitivity can be increased with the increase of RH. Third, response linearity can be improved in the presence of water vapor.

Figure 11:
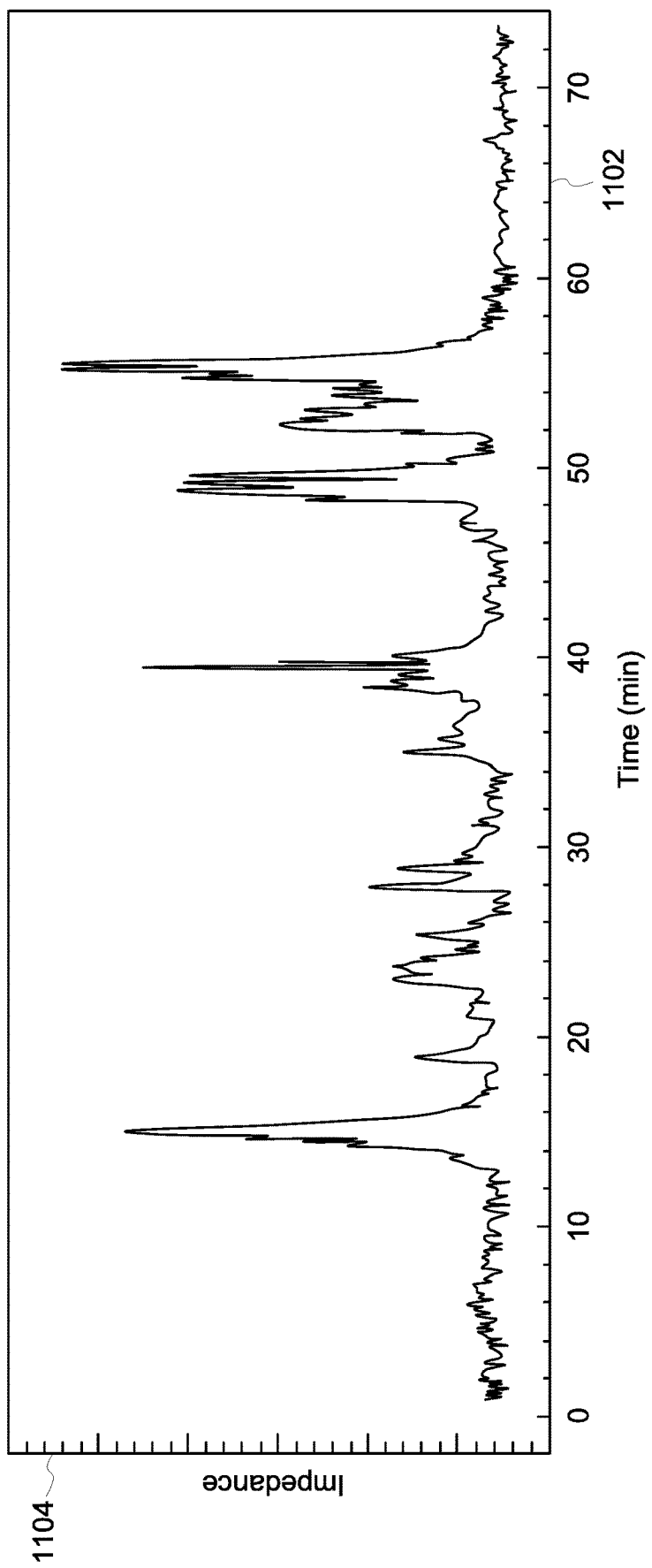
FIG. 11 illustrates graphical illustrations of operation of a multi-gas monitor under dynamic wind conditions in accordance with one embodiment.

In another experiment, measurements of the response of the multi-gas monitor to methane gas were performed outdoors under dynamic field conditions. FIG. 11 illustrates graphical results of monitoring of dynamic methane plumes outdoors using the developed multi-gas monitor. Uncontrolled wind conditions can produce a response pattern of the monitor that can be affected by variable wind direction and variable wind speed. As a result, detected gas concentrations can be the result of convolution between variable wind direction and wind speed. Thus, such results can provide the knowledge about maximum concentrations of gas that reach the detector at certain times.

In one or more embodiments of the subject matter described herein, a multi-gas sensing system includes a sensing circuit comprising one or more sensing elements. Each of the one or more sensing elements includes a sensing material configured to detect at least one gas analyte. A management circuit is configured to excite the one or more sensing elements with an alternating current at at least one predetermined frequency. The management circuit measures one or more electrical responses of the one or more sensing elements responsive to exciting the one or more sensing elements with the alternating current at the at least one predetermined frequency. The management circuit determines one or more characteristics of the sensing circuit. One or more processors receive the one or more electrical responses of the one or more sensing elements and the one or more characteristics of the sensing circuit. The one or more processors determine a concentration of the at least one gas analyte based on the one or more electrical responses of the one or more sensing elements and the one or more characteristics of the sensing circuit.

Optionally, the management circuit may manage a configuration of the one or more sensing elements, and the one or more processors may determine a state of the sensing circuit based on the configuration of the one or more sensing elements.

Optionally, the one or more characteristics of the sensing circuit includes one or more of a temperature of the one or more sensing elements, a state of the sensing circuit based on a configuration of the one or more sensing elements, or one or more ambient conditions proximate the sensing circuit.

Optionally, the sensing circuit may include a heating element. The management circuit is configured to manage a temperature of the one or more sensing elements by controlling the heating element.

Optionally, the one or more processors may determine the concentration of the at least one gas analyte based on the one or more electrical responses of the one or more sensing elements operated at a constant temperature.

Optionally, the management circuit may synchronize the temperature of the one or more sensing elements with the excitation of the one or more sensing elements with the alternating current at the at least one predetermined frequency.

Optionally, the one or more processors may receive information about one or more ambient conditions proximate the sensing circuit. The one or more processors may determine the concentration of the at least one gas analyte based on the one or more ambient conditions.

Optionally, the sensing circuit may be a resistor-capacitor sensing circuit.

Optionally, the sensing circuit may include a transducer and a heating element. The one or more sensing elements, the sensing material, the transducer, and the heating element may be disposed within a common housing.

Optionally, the one or more processors may determine the concentration of the at least one gas analyte based on electrical responses from two or more of the one or more sensing elements. A first sensing element may be operated at a first constant temperature, and a second sensing element may be operated at a second constant temperature.

Optionally, the one or more processors may determine the concentration of the at least one gas analyte based on electrical responses from two or more of the one or more sensing elements. A first sensing elements may be operated at periodically variable temperatures, and a second sensing element may be operated at different periodically variable temperatures.

Optionally, the one or more processors may determine the concentration of the at least one gas analyte based on electrical responses from one of the one or more sensing elements. The one sensing element may be operated at periodically variable temperatures.

Optionally, the one or more processors may determine a baseline correction of the one or more electrical responses responsive to exciting the one or more sensing elements with the alternating current at the at least one predetermined frequency based on the one or more characteristics of the sensing circuit.

Optionally, the one or more processors may dynamically change a selectivity of the sensing circuit.

Optionally, the one or more processors may dynamically change one or more of a selectivity or a sensitivity of the sensing circuit.

Optionally, the one or more processors may determine the concentration of the at least one gas analyte based on a multivariable transfer function.

Optionally, the multivariable transfer function may be based on one or more of the one or more electrical responses of the one or more sensing elements or the one or more characteristics of the sensing circuit.

Optionally, the multi-gas sensing system may be wearable, stationary, mobile, or airborne.

Optionally, the wearable multi-gas sensing system may be held within a wearable or non-wearable transferable object.

Optionally, the system may include a gas-permeable membrane filter disposed over the one or more sensing elements.

Optionally, the gas-permeable membrane filter may include a fluoropolymer.

Optionally, the sensing material is an n-type semiconducting material, a p-type semiconducting material, or a combination n-type and p-type semiconducting material.

Optionally, the management circuit may excite the one or more sensing elements with the alternating current at the at least one predetermined frequency at a high-frequency shoulder region of a relaxation peak or at a low-frequency shoulder region of the relaxation peak of a semiconducting material.

In one or more embodiments of the subject matter described herein, a multi-gas sensing system includes a sensing circuit comprising plural sensing elements. Each of the sensing elements includes a sensing material configured to detect at least one gas analyte. A first element includes sensing electrodes coating with the sensing material and positioned on a substrate, and a second sensing element is a mechanical resonator coated with the sensing material. A management circuit is configured to excite the sensing elements with an alternating current at at least one predetermined frequency. The management circuit includes an impedance analyzer configured to measure electrical responses of the sensing elements based on different detection principles. The impedance analyzer measures a response of the first sensing element at one or more frequencies at a dielectric relaxation peak of the sensing material, and the impedance analyzer measures a resonant peak frequency position of the second sensing element.

In one or more embodiments of the subject matter described herein, a multi-gas sensing system includes a sensing circuit comprising one or more sensing elements. Each of the one or more sensing elements includes a sensing material configured to detect at least one gas analyte. A management circuit is configured to excite the one or more sensing elements with an alternating current at at least one predetermined frequency. The management circuit measures one or more electrical responses of the one or more sensing elements responsive to exciting the one or more sensing elements with the alternating current at the at least one predetermined frequency. The management circuit determines one or more characteristics of the sensing circuit. One or more processors receive the one or more electrical responses of the one or more sensing elements and the one or more characteristics of the sensing circuit. The one or more processors determine a concentration of the at least one gas analyte based on the one or more electrical responses of the one or more sensing elements and the one or more characteristics of the sensing circuit. The one or more processors configured to determine whether the concentration of the at least one gas analyte exceeds a predetermined threshold, and determine a responsive action of one or more of an asset or a subject responsive to determining that the concentration of the at least one gas analyte exceeds the predetermined threshold.

As used herein, an element or step recited in the singular and proceeded with the word "a" or "an" should be understood as not excluding plural of said elements or steps, unless such exclusion is explicitly stated. Furthermore, references to "one embodiment" of the presently described inventive subject matter are not intended to be interpreted as excluding the existence of additional embodiments that also incorporate the recited features. Moreover, unless explicitly stated to the contrary, embodiments "comprising," "including," or "having" (or like terms) an element, which has a particular property or a plurality of elements with a particular property, may include additional such elements that do not have the particular property.

As used herein, terms such as "system" or "controller" may include hardware and/or software that operate(s) to perform one or more functions. For example, a system or controller may include a computer processor or other logic-based device that performs operations based on instructions stored on a tangible and non-transitory computer readable storage medium, such as a computer memory. Alternatively, a system or controller may include a hard-wired device that performs operations based on hard-wired logic of the device. The systems and controllers shown in the figures may represent the hardware that operates based on software or hardwired instructions, the software that directs hardware to perform the operations, or a combination thereof.

As used herein, terms such as "operably connected," "operatively connected," "operably coupled," "operatively coupled," "operationally contacted," "operational contact" and the like indicate that two or more components are connected in a manner that enables or allows at least one of the components to carry out a designated function. For example, when two or more components are operably connected, one or more connections (electrical and/or wireless connections) may exist that allow the components to communicate with each other, that allow one component to control another component, that allow each component to control the other component, and/or that enable at least one of the components to operate in a designated manner.

It is to be understood that the subject matter described herein is not limited in its application to the details of construction and the arrangement of elements set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the presently described subject matter without departing from its scope. While the dimensions, types of materials and coatings described herein are intended to define the parameters of the disclosed subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose several embodiments of the inventive subject matter, and also to enable one of ordinary skill in the art to practice the embodiments of inventive subject matter, including making and using any devices or systems and performing any incorporated methods. The patentable scope of the inventive subject matter is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. A multi-gas sensing system comprising:
   a sensing circuit comprising one or more sensing elements, each of the one or more sensing elements comprising a sensing material configured to detect at least one gas analyte;
   a management circuit configured to excite the one or more sensing elements with an alternating current at one or more predetermined frequencies, the management circuit configured to measure one or more electrical responses of the one or more sensing elements responsive to exciting the one or more sensing elements with the alternating current at the one or more predetermined frequencies, the management circuit configured to determine one or more characteristics of the sensing circuit based on the one or more electrical responses of the one or more sensing elements, wherein the one or more characteristics of the sensing circuit comprises a temperature of the one or more sensing elements; and one or more processors configured to receive the one or more electrical responses of the one or more sensing elements and the one or more characteristics of the sensing circuit, wherein the one or more processors are configured to determine a concentration of the at least one gas analyte based on the one or more electrical responses of the one or more sensing elements and the one or more characteristics of the sensing circuit.

2. The multi-gas sensing system of claim 1, wherein the management circuit is configured to manage a resistor-capacitor configuration of the one or more sensing elements, wherein the one or more processors are configured to determine the concentration of the at least one gas analyte based on the resistor-capacitor configuration of the one or more sensing elements.

3. The multi-gas sensing system of claim 1, wherein the one or more characteristics of the sensing circuit includes a state of the sensing circuit based on a configuration of the one or more sensing elements or one or more ambient conditions proximate the sensing circuit.

4. The multi-gas sensing system of claim 1, the sensing circuit further comprising a heating element, wherein the management circuit is configured to manage a temperature of the one or more sensing elements by controlling the heating element.

5. The multi-gas sensing system of claim 4, wherein the one or more processors are configured to determine the concentration of the at least one gas analyte based on the one or more electrical responses of the one or more sensing elements operated at a constant temperature.

6. The multi-gas sensing system of claim 4, wherein the management circuit is configured to synchronize the temperature of the one or more sensing elements with the excitation of the one or more sensing elements with the alternating current at the one or more predetermined frequencies.

7. The multi-gas sensing system of claim 1, wherein the one or more processors are configured to receive information about one or more ambient conditions proximate the sensing circuit, wherein the one or more processors are configured to determine the concentration of the at least one gas analyte based on the one or more ambient conditions.

8. The multi-gas sensing system of claim 1, wherein the sensing circuit is a resistor-capacitor sensing circuit.

9. The multi-gas sensing system of claim 1, the sensing circuit further comprising a transducer and a heating element, wherein the one or more sensing elements, the sensing material, the transducer, and the heating element are disposed within a common housing.

10. The multi-gas sensing system of claim 1, wherein the one or more processors are configured to determine the concentration of the at least one gas analyte based on electrical responses from two or more of the one or more sensing elements, wherein a first sensing element is configured to be operated at a first constant temperature, and a second sensing element is configured to be operated at a second constant temperature.

11. The multi-gas sensing system of claim 1, wherein the one or more processors are configured to determine the concentration of the at least one gas analyte based on the electrical responses from two or more of the one or more sensing elements, wherein a first sensing element is configured to be operated at periodically variable temperatures, and a second sensing element is configured to be operated at different periodically variable temperatures.

12. The multi-gas sensing system of claim 1, wherein the one or more processors are configured to determine the concentration of the at least one gas analyte based on the electrical responses from one of the one or more sensing elements, wherein the one sensing element is configured to be operated at periodically variable temperatures.

13. The multi-gas sensing system of claim 1, wherein the one or more processors are configured to determine a baseline correction of the one or more electrical responses responsive to exciting the one or more sensing elements with the alternating current at the one or more predetermined frequencies based on the one or more characteristics of the sensing circuit.

14. The multi-gas sensing system of claim 1, wherein the one or more processors are configured to dynamically change a selectivity of the sensing circuit.

15. The multi-gas sensing system of claim 1, wherein the one or more processors are configured to dynamically change one or more of a selectivity or a sensitivity of the sensing circuit.

16. The multi-gas sensing system of claim 1, wherein the one or more processors are configured to determine the concentration of the at least one gas analyte based on a multivariable transfer function.

17. The multi-gas sensing system of claim 16, wherein the multivariable transfer function is based on one or more of the one or more electrical responses of the one or more sensing elements or the one or more characteristics of the sensing circuit.

18. The multi-gas sensing system of claim 1, wherein the multi-gas sensing system is one or more of wearable, stationary, mobile, or airborne.

19. The multi-gas sensing system of claim 18, wherein the wearable multi-gas sensing system is held within a transferable object.

20. The multi-gas sensing system of claim 1, further comprising a gas-permeable membrane filter disposed over the one or more sensing elements.

21. The multi-gas sensing system of claim 20, wherein the gas-permeable membrane filter includes a fluoropolymer.

22. The multi-gas sensing system of claim 1, wherein the sensing material is an n-type semiconducting material, a p-type semiconducting material, or a combination of n-type and p-type semiconducting materials.

23. The multi-gas sensing system of claim 1, wherein the management circuit is configured to excite the one or more sensing elements with the alternating current at the one or more predetermined frequencies at a high-frequency shoulder region of a relaxation peak or at a low-frequency shoulder region of the relaxation peak of a semiconducting material.

24. A multi-gas sensing system comprising:
a sensing circuit comprising one or more sensing elements, each of the one or more sensing elements comprising a sensing material configured to detect at least one gas analyte;
a management circuit configured to excite the one or more sensing elements with an alternating current at one or more predetermined frequencies, the management circuit configured to measure one or more electrical responses of the one or more sensing elements responsive to exciting the one or more sensing elements with the alternating current at the one or more predetermined frequencies, the management circuit configured to determine one or more characteristics of the sensing circuit based on the one or more electrical responses of the one or more sensing elements, wherein the one or more characteristics of the sensing circuit comprises a temperature of the one or more sensing elements; and one or more processors configured to receive the one or more electrical responses of the one or more sensing elements and the one or more characteristics of the sensing circuit,
- wherein the one or more processors are configured to determine a concentration of the at least one gas analyte based on the one or more electrical responses of the one or more sensing elements and the one or more characteristics of the sensing circuit,
- wherein the one or more processors are configured to determine whether the concentration of the at least one gas analyte exceeds a predetermined threshold, and wherein the one or more processors are configured to determine a responsive action of one or more of an asset or a subject responsive to determining that the concentration of the at least one gas analyte exceeds the predetermined threshold.

\* \* \* \* \*